US010011649B2

(12) United States Patent
Diehnelt et al.

(10) Patent No.: US 10,011,649 B2
(45) Date of Patent: Jul. 3, 2018

(54) HIGH AFFINITY SYNBODIES FOR INFLUENZA

(71) Applicants: ARIZONA BOARD OF REGENTS ON BEHALF OF ARIZONA STATE UNIVERSITY, Scottsdale, AZ (US); Christopher Diehnelt, Chandler, AZ (US); Nidhi Gupta, Phoenix, AZ (US); Valeriy Domenyuk, Tempe, AZ (US); Zhan-Gong Zhao, Tucson, AZ (US); Stephen Johnston, Tempe, AZ (US)

(72) Inventors: Christopher Diehnelt, Chandler, AZ (US); Nidhi Gupta, Phoenix, AZ (US); Valeriy Domenyuk, Tempe, AZ (US); Zhan-Gong Zhao, Tucson, AZ (US); Stephen Johnston, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 49 days.

(21) Appl. No.: 14/913,089

(22) PCT Filed: Aug. 25, 2014

(86) PCT No.: PCT/US2014/052545
§ 371 (c)(1),
(2) Date: Feb. 19, 2016

(87) PCT Pub. No.: WO2015/031268
PCT Pub. Date: Mar. 5, 2015

(65) Prior Publication Data

US 2016/0207984 A1 Jul. 21, 2016

Related U.S. Application Data

(60) Provisional application No. 61/870,116, filed on Aug. 26, 2013.

(51) Int. Cl.

| | |
|---|---|
| ***C07K 16/28*** | (2006.01) |
| ***A61K 38/00*** | (2006.01) |
| ***A61K 39/395*** | (2006.01) |
| ***A61K 39/00*** | (2006.01) |
| ***G01N 33/53*** | (2006.01) |
| ***C07K 16/10*** | (2006.01) |
| ***C07K 14/11*** | (2006.01) |
| ***C07K 14/00*** | (2006.01) |
| ***G01N 33/569*** | (2006.01) |

(52) U.S. Cl.
CPC ........ *C07K 16/1018* (2013.01); *C07K 14/001* (2013.01); *C07K 14/11* (2013.01); *G01N 33/56983* (2013.01); *A61K 38/00* (2013.01); *C07K 2318/20* (2013.01); *G01N 2333/11* (2013.01); *G01N 2469/10* (2013.01)

(58) Field of Classification Search
CPC ....... C07K 14/70539; G01N 33/56972; G01N 2333/70539; A61K 47/61; A61K 47/6425
See application file for complete search history.

(56) References Cited

U.S. PATENT DOCUMENTS

| | | | |
|---|---|---|---|
| 7,083,970 | B2 | 8/2006 | Schultz et al. |
| 7,524,647 | B2 | 4/2009 | Schultz et al. |
| 2011/0038935 | A1 | 2/2011 | Marasco et al. |
| 2011/0143953 | A1 | 6/2011 | Johnston et al. |
| 2011/0196029 | A1 | 8/2011 | Wu et al. |

FOREIGN PATENT DOCUMENTS

| | | |
|---|---|---|
| WO | 2008048970 | 4/2008 |
| WO | 2009140039 | 11/2009 |
| WO | 2011029008 A2 | 3/2011 |

OTHER PUBLICATIONS

Jonges et al., Influenza Virus Inactivation for Studies of Antigenicity and Phenotypic Neuraminidase Inhibitor Resistance Profiling., Journal of Clinical Microbiology, Mar. 2010, 48(3):928-940.
Tarus et al., Molecular dynamics studies of the nucleoprotein of influenza A virus: role of the protein flexibility in RNA binding., PLoS One, Jan. 2012, 7(1):e30038.
Grund et al., Comparison of hemagglutination inhibition assay, an ELISA-based micro-neutralization assay and colorimetric microneutralization assay to detect antibody responses to vaccination against influenza A H1N1 2009 virus., Journal of Virological Methods, Feb. 2011, 171(2):369-373.
Matrosovich et al., New low-viscosity overlay medium for viral plaque assays., Virology Journal, Aug. 2006, 3(63).
Diehnelt et al., Synbody Ligands for Norovirus Detection and Capture., ASU Biodesign Institute: Center for Innovations in Medicine, Nov. 2012.
Choplin, Computers and the Medicinal Chemist, Quantitative Drug Design (ed, Ramsden), Chapter 17.2 (pp. 34-57), Pergamon Press, 1992.
Kolb et al., Click Chemistry: Diverse Chemical Function from a Few Good Reactions., Angewandte Chemie International Edition., Jun. 2001, 40(11):2004-2021.
Evans, The rise of azide-alkyne 1,3-Dipolar 'click' cycloaddition and its application to polymer science and surface modification., Australian Journal of Chemistry, 2007, 60(6): 384-395.
Liu et al., Generating DNA Synbodies from Previously Discovered Peptides., Chembiochem, Aug. 2011, 12(12):1813-1817.
Domenyuk et al., A Technology for Developing Synbodies with Antibacterial Activity., PLos ONE, Jan. 2013, 8(1): e54162.
Diehnelt et al., Discovery of High-Affinity Protein Binding Ligands—Backwards., PLoS ONE, May 2010, 5(5):e10728.
Uniprot, Q5CSY6, DHHC family palmitoyl.transferases with 4 transmembrane domains., Uniprot.org, retrieved Feb. 22, 2016, <http://www.uniprot.org/uniprot/Q5CSY6.txt?version=56>.
Uniprot, R9LPU2, Uncharacterized protein., Uniprot.org, retrieved Feb. 22, 2016, <http://www.uniprot.org/uniprot/R9LPU2.txt?version=1>.

(Continued)

*Primary Examiner* — Barry A Chestnut
(74) *Attorney, Agent, or Firm* — George A. Leone; Citadel Patent Law

(57) ABSTRACT

Composition of synbodies that bind influenza. The synbodies are composed of two peptides joined on a scaffold.

8 Claims, 21 Drawing Sheets

(56) References Cited

OTHER PUBLICATIONS

Uniprot, EOPFW8, AraC family transcriptional regulator., Uniprot.org, retrieved Feb. 22, 2016, <http://www.uniprot.org/uniprot/EOPFW8.txt?version=14>.

Uniprot, H3SDJO, Linear gramicidin dehydrogenase LgrE., Uniprot.org, retrieved Feb. 22, 2016, <http://www.uniprot.org/uniprot/H3SDJO.txt?version=5>.

Scaffold 1 (Sc1)

Scaffold 2 (Sc2)

HIGH AFFINITY SYNBODIES FOR INFLUENZA

STATEMENT REGARDING FEDERALLY SPONSORED RESEARCH OR DEVELOPMENT

This invention was made with government support under W911 NF-10-1-0299 awarded by the US Army Research Office. The US government has certain rights in the invention.

FIELD OF THE INVENTION

This invention is directed to a composition of synbodies that bind influenza, more particularly, the synbodies are composed of two peptides joined on a scaffold.

BACKGROUND OF THE INVENTION

Influenza is a critical public health concern and each year 3,000-52,000 people die from influenza infection the United States. Influenza is a constantly evolving pathogen that has rapidly developed resistance to currently approved antivirals. Rapid diagnosis and typing of influenza infection plays a vital role in surveillance and use of antiviral therapeutics. Recently, several ELISA kits that use antibodies for influenza detection have been approved for use in point-of-care facilities but there have been concerns with the variability, sensitivity, selectivity and stability of these tests, illustrating the need for additional influenza affinity ligands. Ideally, these ligands could be used in diagnostic and therapeutic applications and should be rapidly produced to keep pace with viral antigenic drift and shift.

International Publication No. WO08/048970, published Apr. 24, 2008, and entitled "Synthetic Antibodies" describes methods for isolating a class of molecules termed synthetic antibodies or synbodies. Synbodies contain at least two compounds, such as short peptides, joined via a linker. Although the affinity of individual compounds for a target is typically weak, the combination of compounds can bind desired target with affinities comparable to antibodies. Synbodies have advantages over antibodies resulting in part from their smaller size. These advantages may include ease of initial isolation, ease and cost of production, and improved tissue penetration. Synbodies, can be developed by linking two low affinity 15-20 amino acid (aa) long peptides to produce a high affinity synbody for a target protein or bacteria.

In general, synbodies comprising affinity elements and linkers that can be synthesized by standard solid phase synthesis techniques can be synthesized either by addition of amino acids or other monomers in a stepwise fashion, or by joining preassembled affinity elements and linkers or other presynthesized subunits. Techniques for stepwise synthesis of peptides and other heteropolymers are described by e.g., Atherton E, Sheppard R C: Solid Phase peptide synthesis: a practical approach. Oxford, England: IRL Press; 1989, and Stewart J M, Young J D: Solid Phase Peptide Synthesis, 2d Ed. Rockford: Pierce Chemical Company; 1984, which are incorporated herein by reference. Examples of conjugation chemistries have been discussed in International Patent Application Publication Nos. WO08/048970 and WO/2009/

140039, published Nov. 19, 2009. The use of "click" chemistry to perform conjugations between biopolymers and other heteropolymers is also described in Kolb et al., Angewandte Chemie-International Edition 2001, 40(11):2004 and Evans, Australian Journal of Chemistry 2007, 60(6): 384-395, which are incorporated herein by reference.

BRIEF SUMMARY OF THE INVENTION

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, an agent comprises a first peptide having an amino acid sequence comprising a first mutant of SEQ. ID NO: 1 and a second mutant of SEQ ID NO: 1, wherein the first and second mutants are linked and consist of linked mutant peptides SEQ. ID NO: 2-SEQ. ID NO: 2, SEQ. ID NO: 3-SEQ. ID NO: 3, SEQ. ID NO: 5-SEQ. ID NO: 5, SEQ. ID NO: 7-SEQ. ID NO: 7, SEQ. ID NO: 8-SEQ. ID NO: 8, SEQ. ID NO: 9-SEQ. ID NO: 9, SEQ. ID NO:10-SEQ. ID NO: 10, SEQ. ID NO: 11-SEQ. ID NO: 11, SEQ. ID NO: 12-SEQ. ID NO:12, or SEQ. ID NO: 15-SEQ. ID NO: 15.

In another embodiment, the first and second mutant peptides are linked to a scaffold structure to synthesize a composition having an affinity for a target molecule.

In another embodiment, the synthesized composition has an affinity for influenza viruses.

In another embodiment, the scaffold structure has the structure:

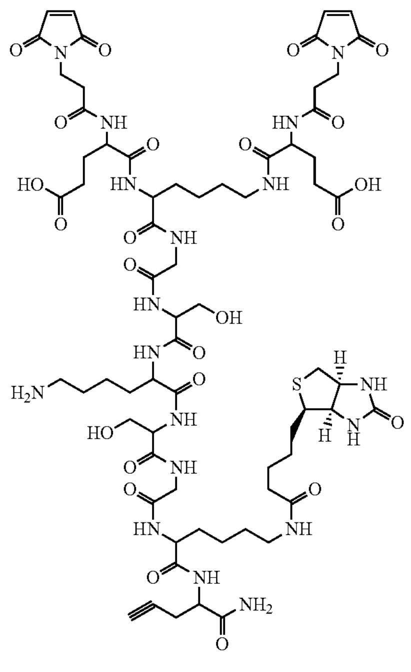 [SMILES: C#CCC(NC(=O)C(CCCCNC(=O)CCCC[C@H]1SC[C@H]2NC(=O)N[C@H]21)NC(=O)CNC(=O)C(CO)NC(=O)C(CCCCN)NC(=O)C(CO)NC(=O)CNC(=O)C(CCCCNC(=O)C(CCC(=O)O)NC(=O)CCN1C(=O)C=CC1=O)NC(=O)C(CCC(=O)O)NC(=O)CCN1C(=O)C=CC1=O)C(N)=O]

In another embodiment, the scaffold structure has the structure:

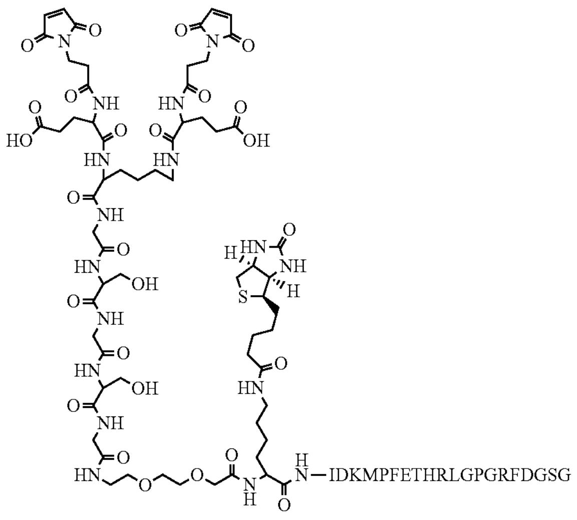

In another embodiment, a composition comprises or consists of SEQ. ID NO: 2, SEQ. ID NO: 3, SEQ. ID NO: 4, SEQ. ID NO: 5, SEQ. ID NO: 6, SEQ. ID NO: 7, SEQ. ID NO: 8, SEQ. ID NO: 9, SEQ. ID NO: 10, SEQ. ID NO: 11, SEQ. ID NO: 12, SEQ. ID NO: 13, SEQ. ID NO: 14 or SEQ. ID NO: 15.

In another embodiment, a composition comprises or consists of the structure

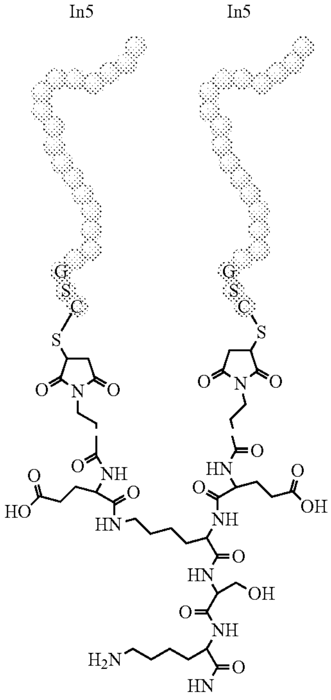

-continued

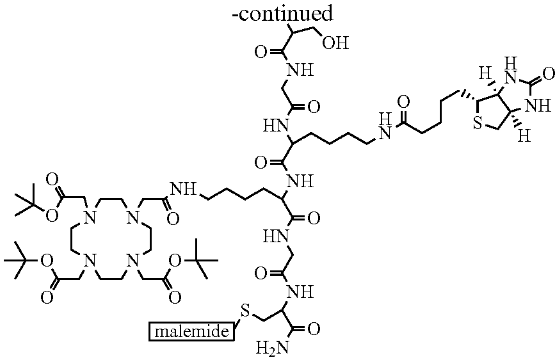

where In5 comprises or consists of SEQ ID NO: 2, SEQ. ID NO: 3, SEQ. ID NO: 4, SEQ. ID NO: 5, SEQ. ID NO: 6, SEQ. ID NO: 7, SEQ. ID NO: 8, SEQ. ID NO: 9, SEQ. ID NO: 10, SEQ. ID NO: 11, SEQ. ID NO: 12, SEQ. ID NO: 13, SEQ. ID NO: 14 or SEQ. ID NO: 15.

In another aspect, a method of detecting an influenza virus, comprises contacting a sample suspected of containing influenza virus with an agent of claim 1, and measuring binding of the agent to the sample compared with a control lacking influenza virus, an increase in binding relative to the control providing an indication of presence of influenza virus.

In another aspect, the sample is from a patient.

In another aspect, the agent further comprises a therapeutic molecule linked to the agent.

In another aspect, a method of diagnosing a patient for an influenza virus, comprises contacting a sample suspected of containing influenza virus with a synthesized agent, and measuring binding of the agent to the sample compared with a control lacking influenza virus, an increase in binding relative to the control providing an indication of presence of influenza virus.

In another aspect, the agent further comprises a therapeutic molecule linked to the agent.

In another aspect, a method of detecting an influenza virus, comprises contacting a sample suspected of containing influenza virus with a composition having a synthesized agent and scaffold structure, and measuring binding of the composition to the sample compared with a control lacking influenza virus, an increase in binding relative to the control providing an indication of presence of influenza virus.

In another aspect, the sample is from a patient.

In another aspect, the agent further comprises a therapeutic molecule linked to the agent.

In another aspect, a method of diagnosing a patient for an influenza virus, comprising contacting a sample suspected of containing influenza virus with a synthetic composition comprising In5, and measuring binding of the composition to the sample compared with a control lacking influenza virus, an increase in binding relative to the control providing an indication of presence of influenza virus.

In another aspect, the agent further comprises a therapeutic molecule linked to the agent.

In another aspect, a diagnostic agent for influenza comprising a first peptide having an amino acid sequence comprises a first mutant of SEQ. ID NO: 1 and a second mutant of SEQ ID NO: 1, wherein the first and second mutants are linked and consist of linked mutant peptides SEQ. ID NO: 2-SEQ. ID NO: 2, SEQ. ID NO: 3-SEQ. ID NO: 3, SEQ. ID NO: 5-SEQ. ID NO: 5, SEQ. ID NO: 7-SEQ. ID NO: 7, SEQ. ID NO: 8-SEQ. ID NO: 8, SEQ. ID NO: 9-SEQ. ID NO: 9, SEQ. ID NO: 10-SEQ. ID NO: 10, SEQ. ID NO: 11-SEQ. ID NO: 11, SEQ. ID NO: 12-SEQ. ID NO: 12, or SEQ. ID NO: 15-SEQ. ID NO: 15;

wherein the first and second mutant peptides are linked to a scaffold structure to synthesize a composition having an affinity for influenza viruses; and wherein contacting a sample suspected of containing influenza virus with the synthesized composition, and measuring binding of the synthesized composition to the sample compared with a control lacking influenza virus, an increase in binding relative to the control providing an indication of presence of influenza virus.

In yet another aspect, a therapeutic agent for influenza comprises a first peptide having an amino acid sequence comprising a first mutant of SEQ. ID NO: 1 and a second mutant of SEQ ID NO: 1, wherein the first and second mutants are linked and consist of linked mutant peptides SEQ. ID NO: 2-SEQ. ID NO: 2, SEQ. ID NO: 3-SEQ. ID NO: 3, SEQ. ID NO: 5-SEQ. ID NO: 5, SEQ. ID NO: 7-SEQ. ID NO: 7, SEQ. ID NO: 8-SEQ. ID NO: 8, SEQ. ID NO: 9-SEQ. ID NO: 9, SEQ. ID NO: 10-SEQ. ID NO: 10, SEQ. ID NO: 11-SEQ. ID NO: 11, SEQ. ID NO: 12-SEQ. ID NO: 12, or SEQ. ID NO: 15-SEQ. ID NO: 15;

wherein the first and second mutant peptides are linked to a scaffold structure to synthesize a composition having an affinity for influenza viruses; and wherein the agent further comprises a therapeutic molecule linked to the synthesized composition.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

Figure 1:
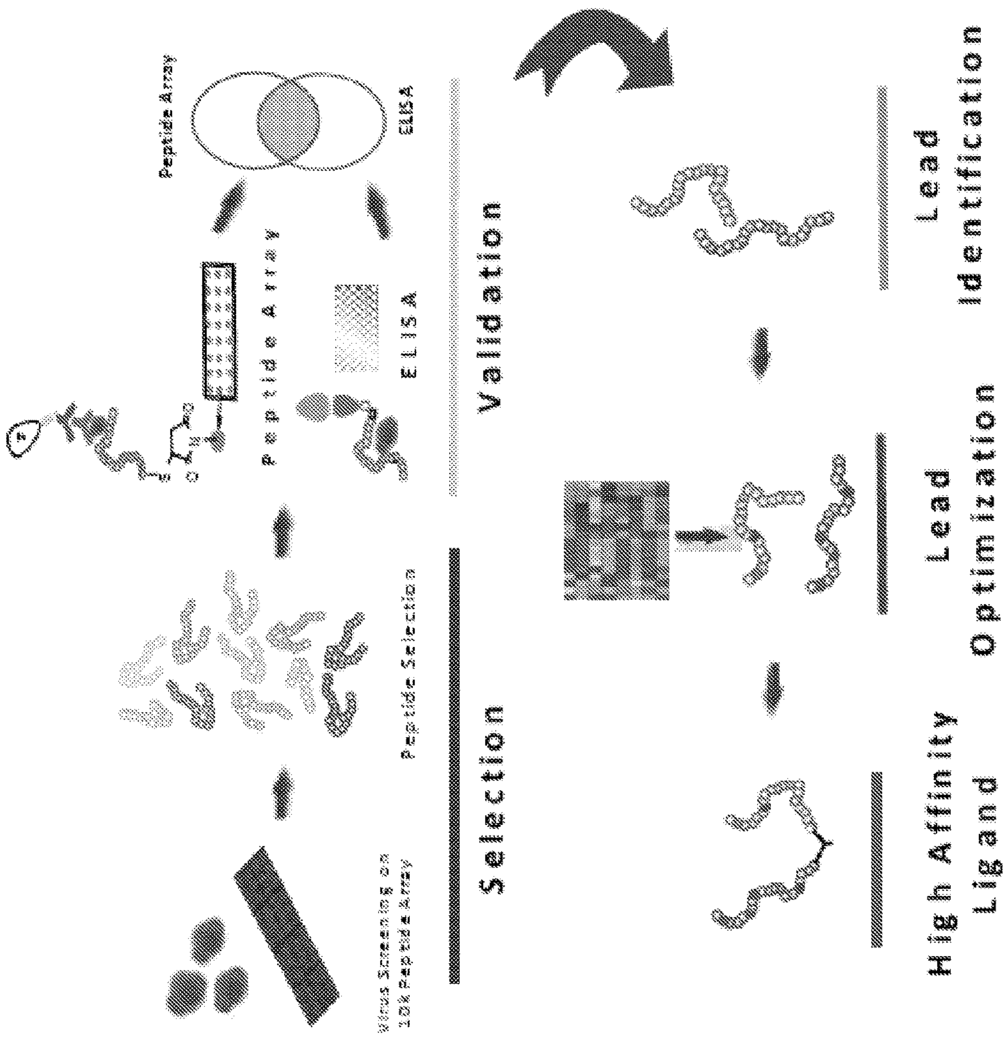
FIG. 1 shows an overview of an example of high affinity synbody development process.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE INVENTION

This disclosure describes the discovery of peptide affinity reagents (synbodies) for influenza virus. Several features of compositions, methods and systems in accordance with example embodiments are set forth and described in the Figures. It will be appreciated that methods and systems in accordance with other example embodiments can include additional procedures or features different than those shown in the Figures. Example embodiments are described herein with respect to an affinity reagent for influenza viruses. However, it will be understood that these examples are for the purpose of illustrating the principles, and that the invention is not so limited. Additionally, methods and systems in accordance with several example embodiments may not include all of the features shown in the Figures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

A synbody is a synthetic entity having at least three components, two of which are compounds having affinity for the same target molecule albeit at different sites within the target molecule and the third being a linker connecting the compounds. The molecular weight of a synbody is usually 500-10,000 kDa and sometimes between about 4 and 5 kDa.

A linker indicates a moiety or group of moieties that connects two or more discrete compounds in a synbody. A linker is typically bifunctional (i.e., the linker contains a functional group at each end that is reactive with groups located on the compounds to be attached). Linkers include amino acids, polypeptides, nucleic acids, small molecules, polymers and particles. Linkers can be linear or branched. Particles serving as linkers or linkers attached to multiple copies of the compounds forming a synbody are sometimes referred to as scaffolds.

A spacer is a molecule optionally present between a linker and a compound attached to the linker. A spacer can be, for example, one or more amino acids or a small organic structure conjugating the linker to a compound.

In some synbodies, the demarcation of compounds, linker and spacer(s) if present is readily apparent, because each has a contiguous or regularly repeating structure distinct from another, or because of conjugation chemistries indicating the points of demarcation. However, a precise understanding of demarcation between these components is not usually necessary for use.

An isolated peptide or other moiety means that the moiety if found in nature is separated at least in part from the molecules with which it is naturally associated including flanking sequences if the peptide is part of a longer protein. If the peptide or moiety is synthetic, isolated means separated at least in part from chemicals used in its production. An isolated peptide does not exclude the presence of heterologous components, such as a linker, second peptide or pharmaceutical excipients not naturally associated with the peptide or used in its synthesis. An isolated moiety can also be pure (e.g., at least 50, 75, 90 or 99% w/w pure) of contaminants Unnatural amino acids are amino acids other than the twenty naturally occurring amino acids that are the building blocks for all proteins, but are nonetheless capable of being biologically or chemically engineered such that they are incorporated into proteins. Unnatural amino acids include D-amino acids, β amino acids, and various other "designer" amino acids (e.g., β-methyl amino acids, Cα-methyl amino acids, and Nα-methyl amino acids). Synthetic amino acids include ornithine for lysine, and norleucine for leucine or isoleucine. Hundreds of different amino acid analogs are commercially available from e.g., PepTech Corp., Mass. In general, unnatural amino acids have the same basic chemical structure as a naturally occurring amino acid, i.e., a carbon that is bound to a hydrogen, a carboxyl group, an amino group, and an R group. Methods of making and introducing a non-naturally-occurring amino acid into a protein are known. See, e.g., U.S. Pat. Nos. 7,083,970; and 7,524,647.

Derivatives should have a stabilized electronic configuration and molecular conformation that allows key functional groups to be presented to the target binding sites in substantially the same way as the lead multimer. Identification of derivatives can be performed through use of techniques known in the area of drug design. Such techniques include self-consistent field (SCF) analysis, configuration interaction (CI) analysis, and normal mode dynamics analysis. Computer programs for implementing these techniques are readily available. See Rein et al., Computer-Assisted Modeling of Receptor-Ligand Interactions (Alan Liss, N.Y., 1989). Derivatives may have higher binding affinity, smaller size, and/or improved stability relative to a lead multimer. Modifications can include N terminus modification, C terminus modification, peptide bond modification, including, $CH_2$—NH, $CH_2$—S, $CH_2$—S═O, O═C—NH, $CH_2$—O, $CH_2$—$CH_2$, S═C═NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference.

Specific binding refers to the binding of a compound to a target (e.g., a component of a sample) that is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however imply that a compound binds one and only one target. Thus, a compound can and often does show specific binding of different strengths to several different targets and only nonspecific binding to other targets. Preferably, different degrees of specific binding can be distinguished from one another as can specific binding from nonspecific binding. The peptides and synbodies of the invention show specific binding to influenza viruses. Specific binding of synbodies of the invention usually involves an association constant of $10^7$, $10^8$ or $10^9$ $M^{-1}$ or higher.

Abbreviations

Enzyme-linked immunosorbent assay (ELISA) is a test that uses antibodies and color change to identify a substance.

"Human Influenza A Virus" is abbreviated "IAV."

"Influenza virus nucleoprotein" is abbreviated "NP."

"Neuraminidase" is abbreviated "NA."

"XTT" is an abbreviation for tetrazolium dye which is commercially available for use in assay protocols including cytotoxicity, and apoptosis assays N,N-Dimethylformamide (DMF), Trifluoroacetic acid (TFA), Acetonitrile (AcCN), Methyl alcohol (MeOH), Dichloromethane (DCM), 1-Hydroxybenzotriazole (HOBt), 2-(1-H-benzotroazole-1-yl)-1,3,3-tetramethyluronium Hexafluorophosphate (HBTU), Nmethylmorpholine (NMM), Trifluoroacetic acid (TFA), N,N-Diisopropylethylamine (DIPEA), Triisopropylsilane (TIPS), 3,6-Dioxa-1,8-octane-dithiol (DoDt), 1-(4,4-Dimethyl-2,6-dioxocyclohexylidene)-3-methyl-butyl (ivDde), Fluorenylmethoxycarbonyl (Fmoc), Kaiser reagents (1. Ninhydrine solution; 6% in ethanol, 2. Potassium cynide in pyridine, 3. Phenol in 80% ethanol) Carboxymethyldextran (CMD). All the regents were used as provided by vendor unless specified.

It has been successfully demonstrated that high affinity ligands (or synbodies) to any given target protein can be prepared by linking low affinity 15-20 AA long peptides. The present disclosure demonstrates the extension of this simple, robust platform technology for rapid production of high affinity ligands for viruses. To explore this concept on viruses, one of the laboratory strains—Influenza A/PR/8/34 was selected.

Referring now to FIG. 1, there shown is an overview of an example of high affinity synbody development process. In one example, a target virus was screened over a small library of 10,000 random peptides (CIM10K) to identify lead peptides with moderate affinity for a target virus and constrained on a scaffold is shown. As described herein, simple bivalent linking can produce a 10 to 100-fold improvement in binding affinity over the starting peptides and this should convert two peptides with modest binding affinity into a high affinity ligand without having prior knowledge of the binding sites and can extend to viruses and thus help in making high affinity ligands without prior knowledge of virus genetics.

A peptide microarray platform for the selection of peptide candidates for any given target including but not limited to proteins, pathogen, cells, and antibodies was established. A library of 10,000 random sequences of 20 mer peptides containing completely random 17 AA positions and three amino acids (G, S, C) linker at the N-terminus were immobilized in array format. Cysteine at N-terminus was used for surface immobilization through reactive sulfhydryl group and has added advantages including, (a) only complete synthesized peptide sequences will be immobilized on the surface, and (b) increased protease stability of the synbody due to amide bond at the N-terminus. Virus particles ($10^8$ virus/slide) were screened on a microarray and antibody based detection methodology was used in screening. Both primary and secondary antibodies were screened as controls to remove false positives in the selection process. Selected peptides as listed in Table 1 were validated in ELISA binding assay before multivalent affinity ligand (synbody) synthesis.

TABLE 1

List of Influenza Binding Peptides

| SEQ ID NO: | Peptide Name | Peptide Sequence |
|---|---|---|
| 1 | P-5 (In5) | CSGDMYEYNPFQGNHIYNKK |
| 16 | P-75 | CSGDSPMGYYHQKTSPWADK |
| 17 | P-204 | CSGQFSAKKYWEIKPMDYWK |
| 18 | P-210 | CSGQYSQQSSSYGQQMFKKE |
| 19 | P-54 | CSGAQEWAAKSYKWNKDGYL |
| 20 | P-68 | CSGDMHWGYQDGKTLVPTSK |
| 21 | P-71 | CSGDPTHATEPKRYEAYNDH |
| 22 | P-88 | CSGEMWAIMPPIIKPDNKGH |
| 23 | P-125 | CSGHNIYAQYGYPYDHMYEG |
| 24 | P-134 | CSGKDHNAQDQESVHWKYKG |
| 25 | P-147 | CSGKRYLQKGKGALRGLYIF |
| 26 | P-149 | CSGKSQEIGDPDDIWNQMKW |
| 27 | P-150 | CSGKTEHYMPNNNTFGYEYE |

TABLE 1-continued

List of Influenza Binding Peptides

| SEQ ID NO: | Peptide Name | Peptide Sequence |
|---|---|---|
| 28 | P-157 | CSGLLHELPDDYEKINPQKY |
| 29 | P-158 | CSGLLYHFKVGLRTMKISMM |
| 30 | P-166 | CSGMKQPKHNKINDNPKAYE |
| 31 | P-174 | CSGNETAPDNTYRYKQSAQK |
| 32 | P-227 | CSGSFNQEYFPYPMIDYLKK |
| 33 | P-241 | CSGTANELLYYKNYGVKNPK |
| 34 | P-243 | CSGTEEKYINDSNFADEKGH |

With an aim to develop ligands with high affinity influenza, one objective was to improve lead peptides affinity for Influenza A/PR8/34. We selected one of the lowest binding peptides (P5) for binding affinity improvement. one of the lowest binding peptide (In5) was selected for binding affinity improvement. Due to the linear nature of most of the 20 AA peptides, it is possible to make single AA substitutions to identify AA's that increase affinity. These identified AA substitutions were added in combination of 5-8 AA acids to design a new peptide sequence with possible improved binding. Taking advantage of this platform, D-amino acids substitutions were used to increase protease stability in downstream applications. For this, each amino acid in the lead peptide sequence was replaced with 19 D-AA's (a, r, n, d, e, q, g, h, i, l, k, m, f, p, s, t, w, y, v) to design an amino acid point variant peptide library containing 324 peptides for the selected lead peptide (P5). Microarrays with 324 peptides were screened and analyzed similar to CIM10 k microarrays. A heat map was generated by calculating relative valves with respect to lead P5 which clearly showed the effect of each AA substitution in the lead sequence. A single amino acid substitution with arginine or proline in place of glutamic acid alone gave 40-60 fold improvements in binding over original sequence. Also, arginine substitution at aspartic acid or asparagine position improved affinity 20-60 fold. On the basis of these results a plurality of new optimized peptides, listed in Table 2, were designed and synthesized by addition of 5-6 amino acid combinations using arginine, proline, and lysine. These new optimized peptides were synthesized and directly used for synbody construction on a bivalent scaffold.

TABLE 2

List of designed mutant peptides for peptide (In5)

| SEQ ID NO: | Peptide Name | Peptide Sequence |
|---|---|---|
| 1 | P-5 (In5) | CSGDMYEYNPFQGNHIYNKK |
| 2 | Opt1 | CSGDMYrYNPFQGNHIYNKK |
| 3 | Opt2 | CSGrMYEYNPFQGNHIYNKK |
| 4 | Opt3 | CSGDMYpYNPFQGNHIYNKK |
| 5 | Opt4 | CSGrMYpYNPFQGNHIYNKK |
| 6 | Opt5 | CSGrMYrYNPFQGNHIYNKK |
| 7 | Opt6 | CSGDMYEYNPFQGNHIYrKK |

TABLE 2-continued

| List of designed mutant peptides for peptide (In5) | | |
|---|---|---|
| SEQ ID NO: | Peptide Name | Peptide Sequence |
| 8 | Opt7 | CSGrMYpYNPFQGNHIYrKK |
| 9 | Opt8 | CSGtMYEYNPFQGNHIYNKK |
| 10 | Opt9 | CSGDMYEYrPFQGNHIYNKK |
| 11 | Opt10 | CSGrMYpYrPFQGNHIYrKK |
| 12 | Opt11 | CSGtMYpYrPFQGNHIYrKK |
| 13 | Opt12 | CSGrMYpYrPFQrkHIYrKK |
| 14 | Opt13 | CCSGDrYEYNPFQGkHIYNK |
| 15 | Opt14 | CSGrMYEYNPFQGkHIYrKK |

Figure 2A:
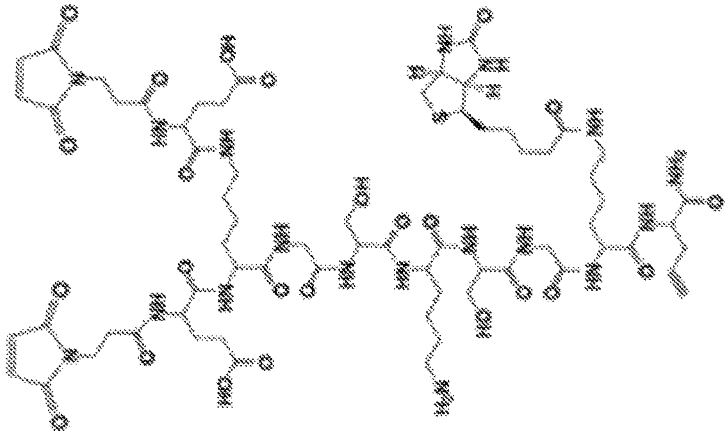
FIG. 2A shows a structure of a first scaffold used to construct influenza binding synbodies.
Figure 2B:
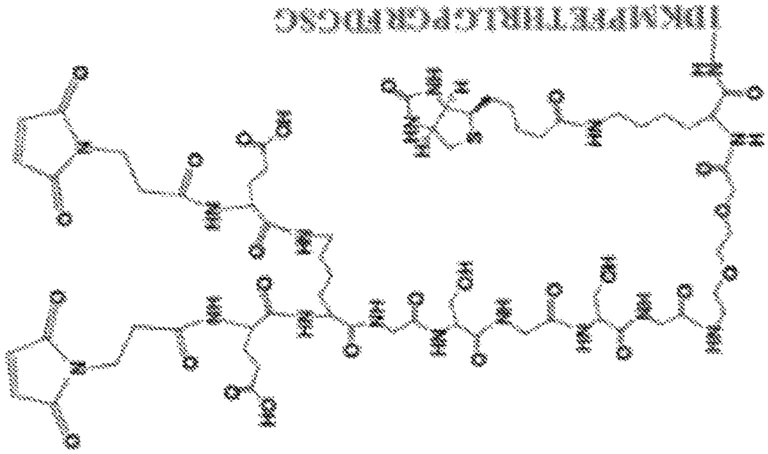
FIG. 2B shows a structure of a second scaffold used to construct influenza binding synbodies.

For synbody construction, two bivalent peptide based scaffolds "Scaffold 1 and Scaffold 2" (as shown in FIG. 2A and FIG. 2B) were designed with maleimide groups and sulfhydryl conjugation chemistry was chosen to mimic the orientation and chemistry of the peptides on the microarrays. Both the scaffolds and peptides were prepared via standard solid phase peptide chemistry (SPPS). Therefore modifications can be made according to desired applications. Also, glutamic acid and 6 AA sequence (GSGKSG (SEQ ID NO: 35)) were added to increase solubility as well as for easy detection on MALDI-TOF for characterization and quality control purposes. The addition of an inert orthogonal group "propargyl glycine" in the scaffold-1 added an extra coupling site for the development of various downstream assays. To test the modularity of the peptide-scaffold linking, designed another scaffold with a peptide IMKPFETHRLGPERFDGSC (SEQ ID NO: 36) attached at the C-terminus and two units of mini-PEG molecule to increase solubility.

The synbodies were synthesized by conjugating peptides with cysteine at N-terminus to maleimide functionalized scaffold at pH 7.0 in presence of TEA. This way amide bond at the C-terminus of the peptide became N-terminus and could be less susceptible to protease cleavage and one of the reason of designing peptide libraries with N-terminus cysteine. Reaction of each peptide with the scaffold results only homo-bivalent synbodies. The synthesized Synbodies were characterized by MALDI-TOF and purified by HPLC for functional assays. The sulfhydryl assisted covalent attachment of cysteine containing peptides to scaffolds is very rapid and scalable with high yields for the fast production of large number of ligands in very short time. In the last 10 years, technical advances in peptides production and scale have increased the economics and eminence of peptides in drug development; making this platform more cost effective comparable to existing ligand discovery and development systems. The homo-bivalent synbody candidates (P-5) prepared on scaffold-1 were screened unpurified and compared for their binding behavior against target virus via surface plasmon resonance (SPR). Four out of fifteen synbodies showed improved binding (Table 2) and identified synbody opt10-opt10 as lead candidate with >100 fold improvement over wild type (WT) (P5-P5) candidate.

TABLE 3

| Synbodies constructed and tested for influenza binding by SPR | | |
|---|---|---|
| SEQ ID NO: | Synbody Name | Fold Change versus WT Synbody |
| | WT | 1 |
| 2-2 | opt1-opt1 | 6 |
| 3-3 | opt2-opt2 | 3 |
| 4-4 | opt3-opt3 | n.b. |
| 5-5 | opt4-opt4 | 10 |
| 6-6 | opt5-opt5 | n.b. |
| 7-7 | opt6-opt6 | 4 |
| 8-8 | opt7-opt7 | 45 |
| 9-9 | opt8-opt8 | 1 |
| 10-10 | opt9-opt9 | 1 |
| 11-11 | opt10-opt10 | 131 |
| 12-12 | opt11-opt11 | 47 |
| 13-13 | opt12-opt12 | n.b. |
| 14-14 | opt13-opt13 | n.b. |
| 15-15 | opt14-opt14 | 107 |

n.b.—no binding

Figure 5:
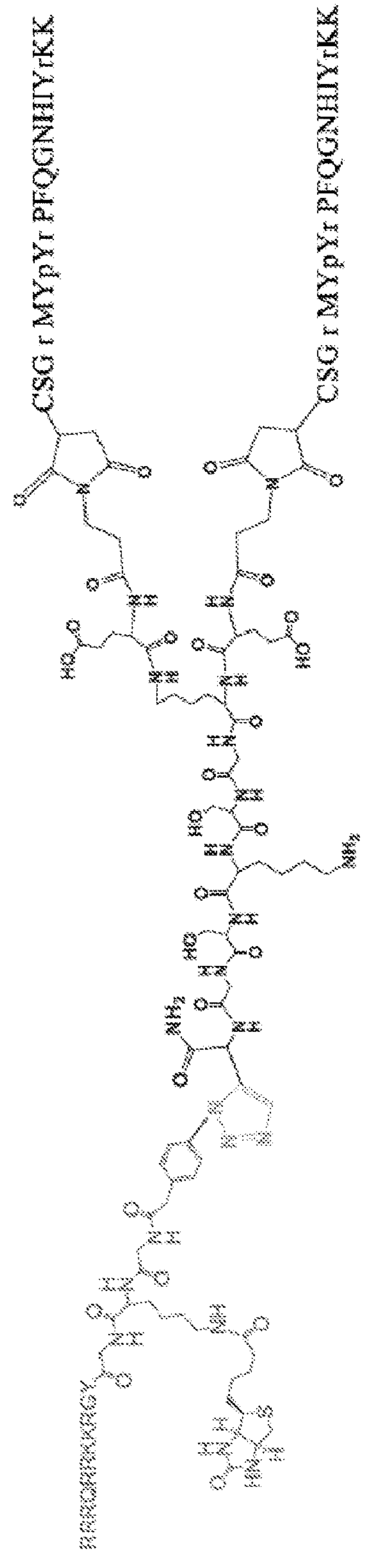
FIG. 5 shows a synthesized synbody conjugated to Tat peptide.

To further ensure the results, purified optimized (opt10-opt10-Sc-1) and wild type (P5-P5-Sc-1) synbody candidates tested along with optimized (opt10) and selected lead (In5) peptides in ELISA binding assay. The optimized peptide showed approximately 1000 fold improvement over identified lead peptide which on linking on either of the scaffolds showed 40 times increment in binding affinity compared to single optimized peptide alone. Overall, in just two steps a 24,000 fold improved optimize synbody was designed with binding affinities (KD=1 nM) which is in range of anti-influenza NA monoclonal antibody (FIG. 5). These results demonstrated that attachment of extra groups/peptides does not affect the binding constant and the modularity of the synbody design that it can be modified for any new application without compromising the binding affinities.

Figure 6:
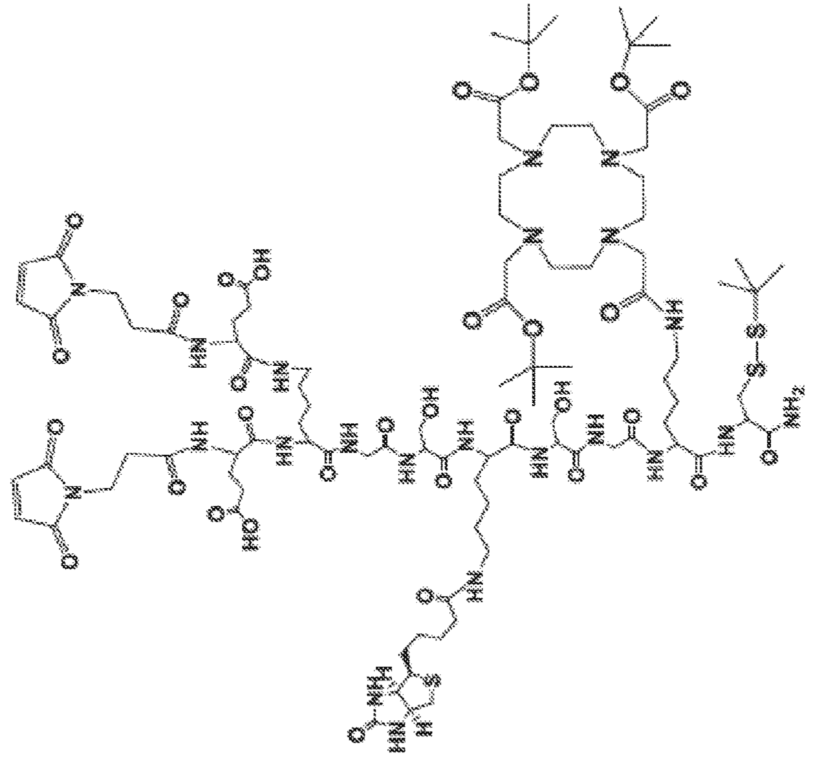
FIG. 6 shows a hypothetical example of a designed synbody with metal chelator macrocyclic species DOTA.
Figure 7:
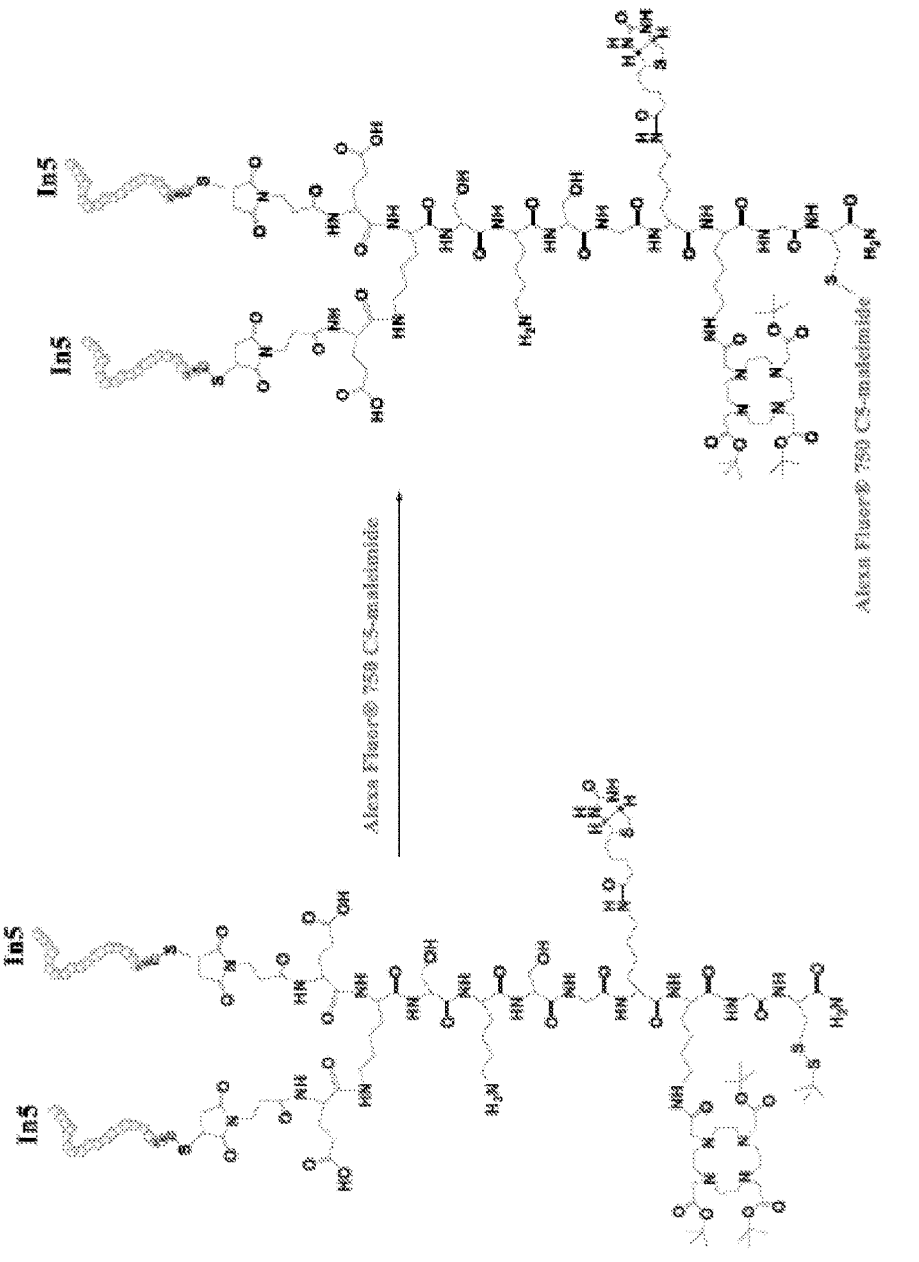
FIG. 7 shows a synbody including linking to peptide In5 labeled and with Alexa dye for in-vivo imaging to study the bio-distribution of the chemical entity.

It is possible that these synbodies could interfere with an influenza infection, therefore, we designed several modifications to the synbody scaffold that can improve the performance or aid in the in vivo characterization of the synbody. It is possible that synbodies can interfere with virus replication inside the cells, therefore we designed a scaffold with a function group whereby it is easy to attach a cell penetrating peptide, such as Tat (illustrated in FIG. 5) to the synbody. It is important to understand the bio-distribution of a potential therapeutic, therefore we designed synbodies with a metal chelator macrocyclic species like DOTA as shown in FIG. 6 and one with an Alexa dye (as shown in FIG. 7) for in-vivo imaging to study the bio-distribution of the chemical entity.

Method to Improve Physiochemical Stability of Synbody Candidates.

Figure 8:
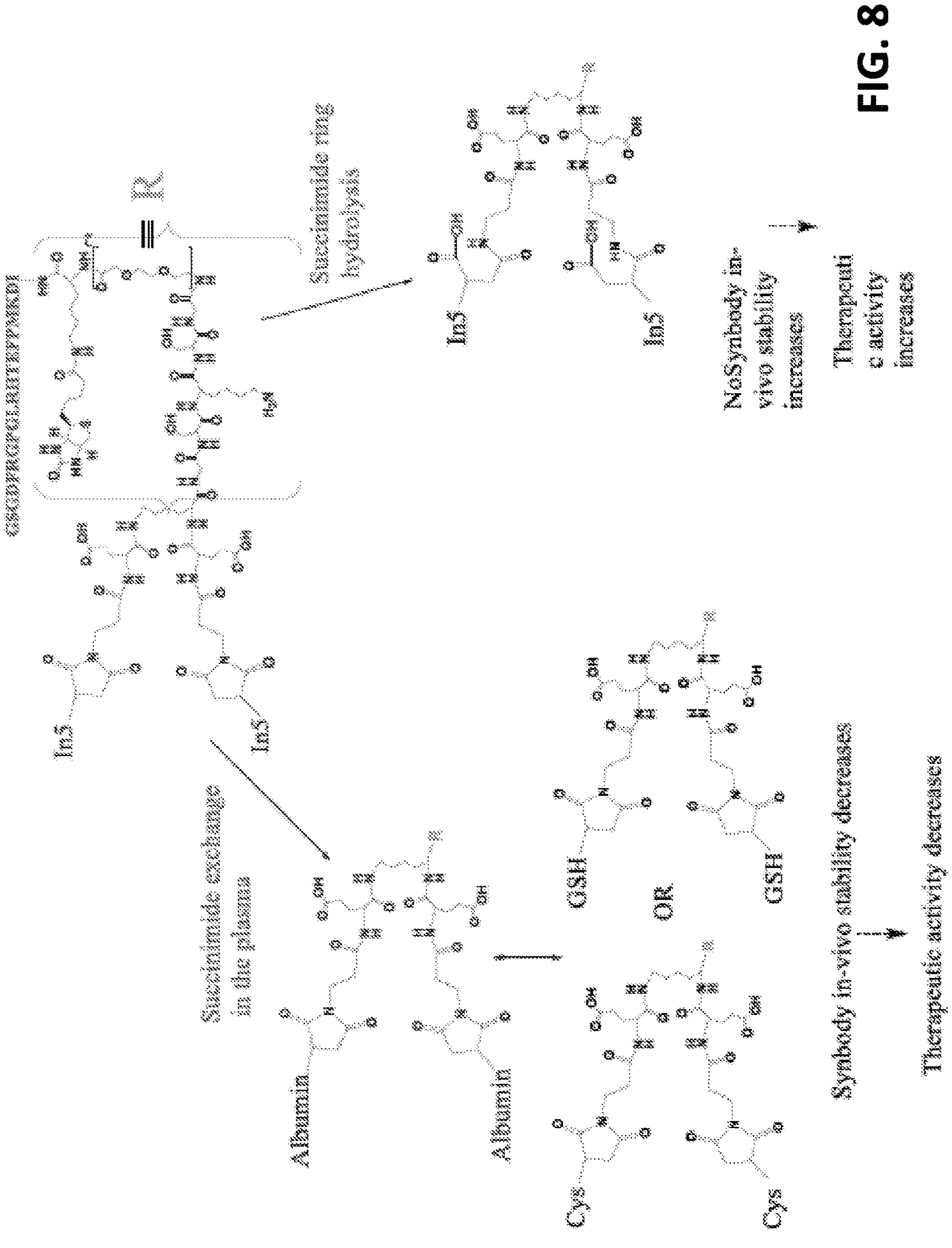
FIG. 8 shows a method for improving physiochemical stability of synbody candidates using hydrolysis.

Referring now to FIG. 8 a method for improving physiochemical stability of synbody candidates using hydrolysis is shown. In this hypothetical example, sulfhydryl conjugation chemistry was selected for rapid production of synbodies. But in in-vivo functional assays, this maleimide coupled synbodies undergoes exchange reaction with albumin, glutathione and other cysteine moieties present in the plasma. This succinimide exchange reaction results in new products formed via sulfhydryl conjugation of scaffold to albumin, glutathione and other cysteine moieties present in the plasma. This led to reduced circulating synbody amount in the plasma. A method to avoid succinimide exchange reaction in-vivo was developed and for this we have hydrolyzed the succinimide ring first before testing in-vivo. This completely inhibits succinimide exchange and desired synbody is circulating without any modifications. This concept has been tested over many synbodies synthesized using maliemide chemistry with different peptide sequences and scaffold types and found that succinimide ring opening totally inhibits sufhydryl exchange and increase circulating synbody half-life in-vivo.

EXAMPLES AND SUPPORTING METHODS

Supporting Method (SM1)—Screening of Influenza A PR/8/34 H1N1 on Peptide Microarray Peptide microarrays were washed with 90% TFA for 5 minutes followed by rinsing with DMF (1×), 95% ethanol (1×), and double-distilled water (ddH2O) (2×). Microarrays were dried by centrifuging at 1500 rpm for 2 minutes. After drying, microarrays were blocked with 600 ul blocking buffer [3% bovine serum albumin (BSA), 0.05% Tween20, 0.134 mg/ml Mercaptohexanol in 1× Tris buffered saline (TBS)] in a humidity chamber for 1 hour at room temperature. After blocking, microarrays were washed with washing buffer (1×TBS+0.05% Tween20) followed by two washes with ddH2O. The following reagent was obtained through the NIH Biodefense and Emerging Infections Research Resources Repository, NIAID, NIH: Influenza A Virus, A/Puerto Rico/8/34 (H1N1), NR-348. Influenza solutions (250 uL) at five different concentrations ($7.5\times10^8$, $1.5\times10^9$, $3\times10^9$, $7.5\times10^9$, $1.5\times10^{10}$ vp/ml) were incubated in competition with protease inhibited bovine serum (5 mg/mL) in Agilent microarray chambers for 1 hour at 37° C. Microarrays were washed as before and probed with 5 nM, 250 uL mouse monoclonal anti-influenza NA (BEI Resources, Cat. No: NR-4540) with same competitor in Agilent microarray chambers for 1 hour at 37° C. Microarrays were washed and probed with 5 nM, 250 uL AlexaFluor-647 conjugated anti-mouse secondary antibody (Life Technologies, Cat. No: A21235) for 1 hour at 37° C. All the slides were washed, dried, and scanned on an Agilent Microarray Scanner. Each sample was run in 4 replicates. As a negative control the primary antibody was screened in absence of pathogen. Data were analyzed with Agilent GeneSpring software without additional normalization.

To select influenza binding peptide candidates, the following selection criteria were used: (a) signal ratio of influenza/antibody only >2 (b) less than 30% deviation between peptide replicates (c) increasing signal with increasing viral concentration. As unpurified peptides were used in the 10K peptide library, this initial list of candidates (114) was filtered by synthesis quality, based on their MALDI mass spectra, in order to eliminate any peptides whose binding might be mediated by unremoved protecting groups. A total of 57 peptides passed this step and were synthesized (Sigma Custom Peptide, The Woodlands, Tex.) with an N-terminal biotin tag for use in subsequent assays.

Supporting Method (SM2)—Screening of Influenza Binding Peptides by Peptide Microarray The selected peptide candidates were printed on polymer slides as in the initial screening but were printed at three different concentrations (~0.5 mg/mL, 1 mg/mL, 2 mg/mL) for the secondary screening. This was done to test that peptide binding from the initial screening was reproducible and that influenza binding occurred at other peptide dilutions. This should reduce the chance that the observed peptide binding was simply a product of avidity of high levels of immobilized peptide. In addition, we compared binding between live H1N1 and H1N1 inactivated by UV (Advanced Biotechnologies, Inc. #10-273-500) or formalin treatment; inactivated following a standard inactivation protocol. Data from the three preparations of influenza binding to the immobilized peptides was very comparable; therefore UV inactivated influenza was used for subsequent assays.

Supporting Method (SM3)—Screening of Influenza Binding Peptides by ELISA

Nunc MaxiSorp flat bottom 96 well ELISA plates (VWR #62409-002) were coated with 50 uL of 0.2 ug/well of UV inactivated Influenza A PR/8/1934 H1N1 in ELISA coating buffer and kept overnight at 4° C. Plates were washed with 1×PBST followed by blocking with 100 uL 3% BSA in 1×PBST for 2 hours at 37° C. After washing plates, biotin labeled peptides were added in a concentration range from 0.39 to 100 uM in dilution buffer [0.1% BSA+1×PBST+0.05% v/v Tween20] and incubated for 1 hour at 37° C. Plates were washed and 100 uL of 1:2000 streptavidin-HRP (Thermo Scientific # N100) was added and incubated for 1 hour at 37° C. Plates were washed and 100 uL of 3,3',5,5'-tetramethylbenzidine (TMB) (Thermo Scientific # N301) was added and incubated in the dark for 15 minutes at room temperature. The reaction was quenched by the addition of 100 ul of 0.5M HCl and read immediately at 450 nm using a microplate reader (Spectra MAX 190, Molecular Devices, Inc.). ELISA dilution buffer was run as control on influenza coated wells. Also, two peptide concentrations 0.39 uM and 100 uM were run on non-influenza coated wells.

Supporting Method (SM4)—Synthesis of Scaffolds (Sc1 and Sc-2)

All the Fmoc-amino acids and coupling reagents were from AAPPTEC (Louisville, Ky.). FmocPal-PEG resin (0.2 mmole/gram) was purchased from Life Technologies (Grand Stateley, N.Y.). Maleimidopropionic acid was from Bachem (Torrance, Calif.). Trifluoroacetic acid (TFA), piperidine, N,N-diisopropylethylamine (DIPEA) were purchased from Spectrum (Los Angeles, Calif.). And remaining reagents/solvents were obtained from Fisher Scientific.

Figure 3A:
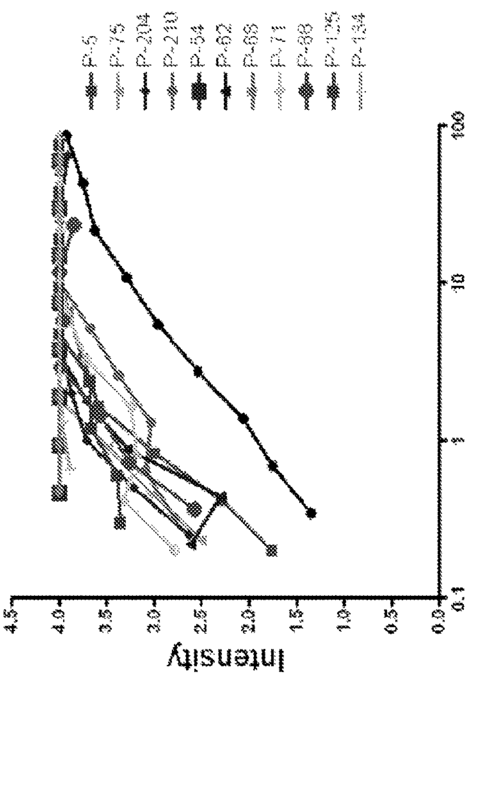
FIG. 3A and FIG. 3B show binding curves of biotin-labeled peptides tested against Influenza coated ELISA plates where peptide concentration is plotted versus A450 (y-axis).
Figure 3B:
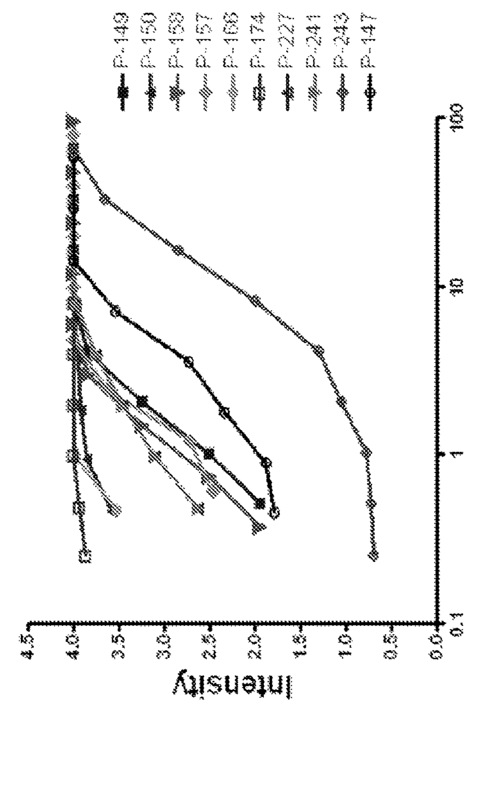

S3 Both scaffolds (Sc1 and Sc2) were synthesized via Fmoc based solid phase peptide synthesis. The synthesis was carried out at 0.5 mmole scale on Fmoc-Pal-PEG resin Rink amide resin (0.2 mmole/g). The sequences are shown in FIG. 3. Following removal of Fmoc-protecting group by 20% piperidine in DMF for 5+15 minutes, the stepwise assembly of the peptide sequence was performed via addition of the appropriate Fmoc protected amino acids. The N-terminus was substituted with maleimide group manually by treating with 5 fold excess of maleimidopropionic acid in the presence of 5 fold excess of HOBt and diisopropylcarbodiimide in DMF. The resin was agitated at room temperature for 1 hour followed by standard washings with DMF (3 times, 1 minute per wash), MeOH (2 times, 1 minute per wash), DCM (2 times, 1 minute per wash), DMF (3 times, 1 minute per wash). An aliquot of resin was taken after MeOH wash for qualitative Kaiser Test. The final protected scaffolds was treated with cleavage cocktail (TFA: H2O: TIPS: 90:5:5) for 2 hours at room temperature and precipitated in cold diethyl ether. The precipitated construct was cooled for 15 minutes in −80° C. refrigerator to ensure complete precipitation. The solid was separated from the diethyl ether by centrifugation and the top phase was decanted off and pellet re-suspended with another addition of dry diethyl ether. The cooling and centrifugation process was done in triplicate. Upon completion, the construct was dried and dissolved in water for HPLC purification. The construct was purified on reverse-phase HPLC (Agilent 1200 Series HPLC) using a Phenomenex Luna 5u semi-preparative (10 mm×250 mm) C-18 column using solvent system A: 0.1% TFA in H2O; solvent B: 90% CH3CN in 0.1% TFA with a linear gradient method, (0 min, 10% B; 2 min, 10% B; 20 min, 45% B; 25 min, 95% B; 27 min, 95% B; 30 min, 100% B; 33 min, 10% B) with flow rate of 4 mL/min at a wavelength of 280 nm. The appropriate fractions were collected and analyzed by MALDI-TOF mass spectrometry. The correct fraction was then lyophilized. These scaffolds were then purchased at large scale (>90% purity) from Sigma Custom Peptide and used for subsequent synbody preparation.

Supporting Method (SM5)—Conjugation of Synbodies

General Method—

In the synthesis of a synbody, the peptide and the scaffold are separately dissolved in 30% acetonitrile in water. One equivalent of the scaffold is first mixed with two equivalents of the peptide; the pH of the reaction mixture is then adjusted to 6.5-7.0 with the addition of dilute triethylamine (TEA) (10% in acetonitrile). The reaction is allowed to proceed at room temperature without shaking and monitored by HPLC and MALDI-MS. The yield of the reaction is determined by integration of the peaks assigned to the desired product.

Example 1

Synbody opt10-opt10-Sc1.

Figure 12:
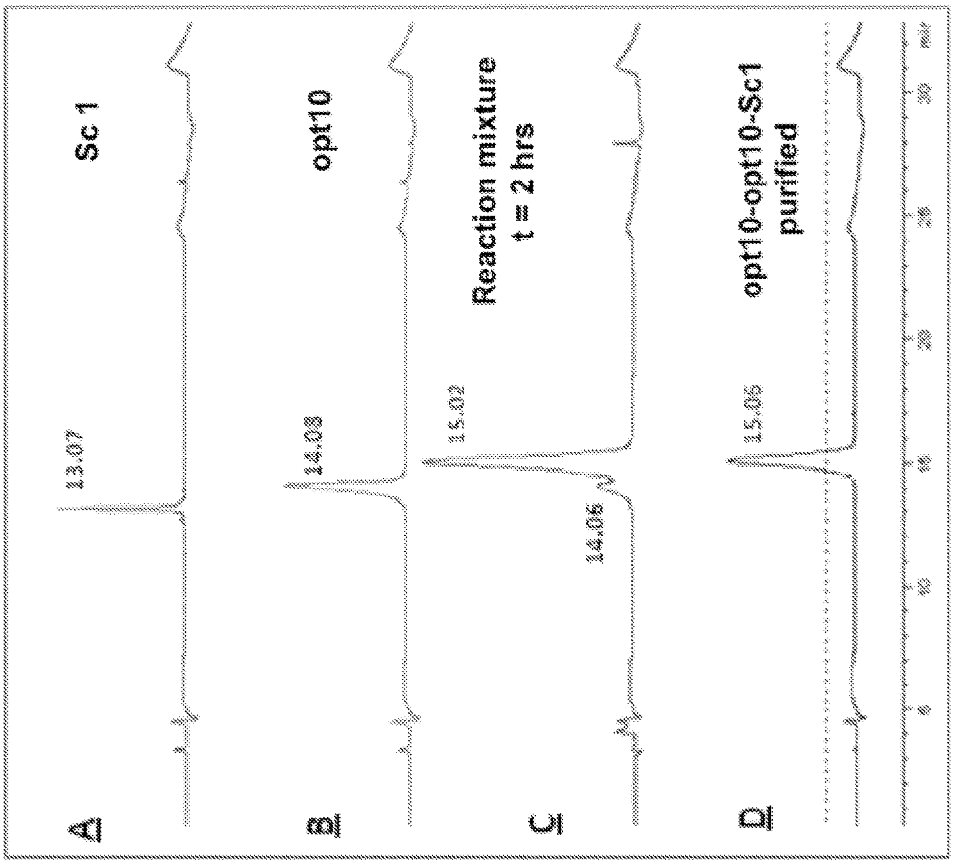
FIG. 12 shows HPLC chromatograms of A) scaffold Sc1, B) opt10 peptide, C) reaction mixture at two hours; and D) purified synbody, opt10-opt10-Sc1.
Figure 13:
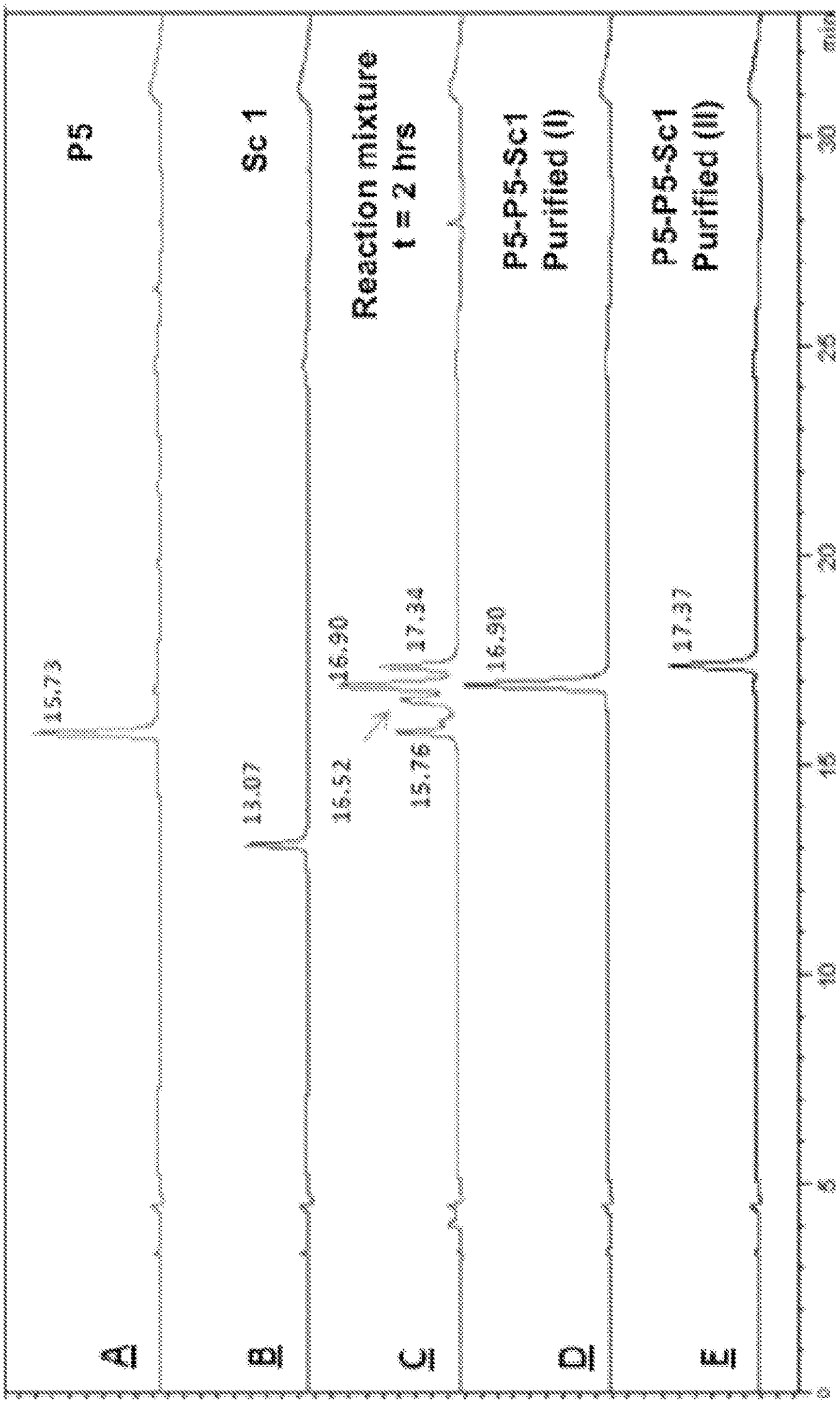
FIG. 13 shows HPLC chromatograms of A) peptide 5 (P5), B) scaffold Sc1, C) reaction mixture at two hours, D) purified P5-P5-Sc1 synbody I, and E) purified P5-P5-Sc1 synbody II.

HPLC analysis of the reaction mixture showed that the scaffold, Sc1, was completely consumed in two hours (FIG. 12). A single peak at 15.02 min corresponded to the desired synbody product. The yield of the desired synbody was estimated as >90% by the integration of the peak. MALDI-MS: calculated for M+H 6570.163 (monoisotopic), found 6572.685. Referring now to FIG. 13 HPLC chromatograms of A) scaffold Sc1, B) opt10 peptide, C) reaction mixture at two hours; and D) purified synbody, opt10-opt10-Sc1 is shown.

Example 2

Synbody opt10-opt10-Sc2.

Figure 14:
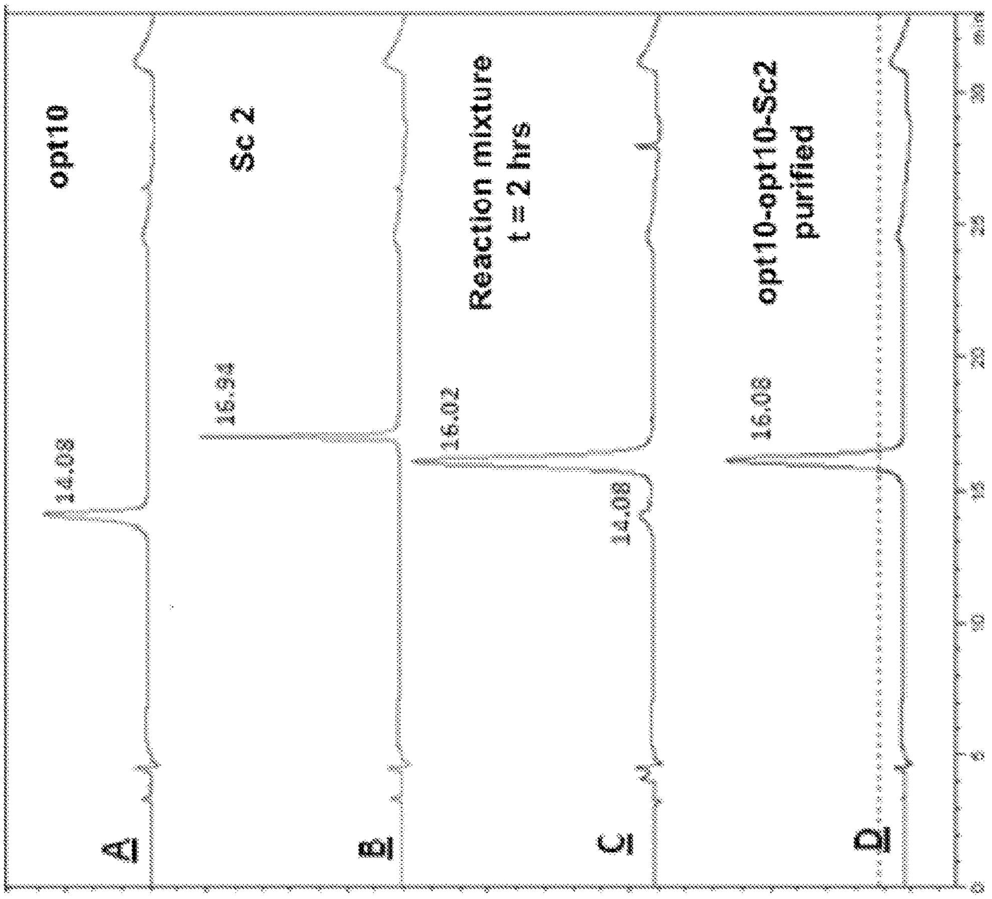
FIG. 14 shows HPLC chromatograms of A) opt10 peptide, B) scaffold Sc2, C) reaction mixture at 2 hours, and D) purified synbody opt10-opt10-Sc2.

HPLC analysis showed that, after two hours of reaction, the scaffold, Sc2, was completely consumed (FIG. 13). The peak at 16.08 min is characterized by MALDI-MS as the desired synbody product, the yield of the desired product was estimated as >90% by HPLC integration. MALDI-MS: calculated for M+H, 8818.239 (monoisotopic), found 8819.824. Referring now to FIG. 14 HPLC chromatograms of A) peptide 5 (P5), B) scaffold Sc1, C) reaction mixture at two hours, D) purified P5-P5-Sc1 synbody I, and E) purified P5-P5-Sc1 synbody II are shown.

Example 3

Synbody P5-P5-Sc1.

Figure 4:
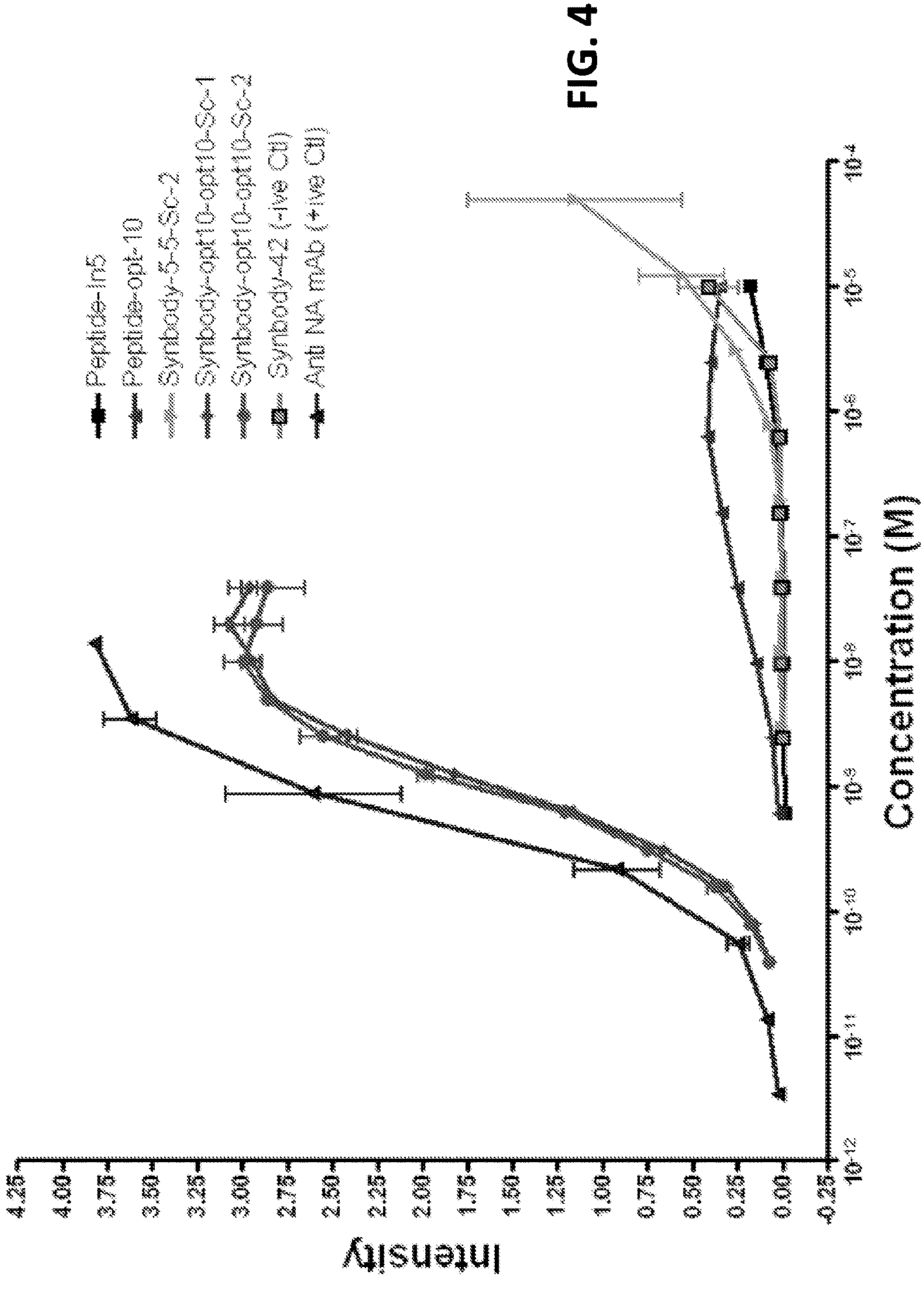
FIG. 4 shows binding curves of In5-In5 and opt10-opt10 synbodies to influenza in ELISA.

HPLC analysis of the reaction showed that the scaffold Sc1, was completely consumed in two hours. However, there were two peaks (t=16.9 min and t=17.34 min) corresponding to the desired product (t=17.34 min), while the peak at 16.52 contains both the mono conjugation of peptide 5 (P5) to Sc1 and the P5-P5-Sc1 synbody. The combined yield of synbody I and II, is determined as 73% based HPLC integration. MALDI-MS: calculated for M+H 6383.731 (monoisotopic), found 6385.485 (synbody I), 6385.096 (synbody II). FIG. 4 shows binding curves of In5-In5 and opt10-opt10 synbodies to influenza in ELISA. Affinity ligand concentration is plotted versus A450 (y-axis).

Supporting Method (SM6)—SPR Screening of Synbodies

Determination of the binding of synbodies to immobilized influenza virus was performed on a Biacore 4000. The series S sensor chip CM5, amine coupling reagents and HBS-EP were obtained from GE Healthcare. An amine immobilization protocol was performed at 25° C. using 10 mM NaHCO3, pH 5.0 as the immobilization buffer. All five spots on one flow cell of the CM-5 chip were activated by a 10 minute injection of a freshly prepared 1:1 solution of 400 mM EDC: 100 mM NHS in water. Spots 1, 2, 4 and 5 were treated with a solution of UV inactivated Influenza A PR8/1934 (50 μg/ml) in 10 mM NaHCO3, pH 5.0 for 8, 14, 16, and 10 minutes at a flow rate of 10 mL/min. Any residual active sites were then quenched by a 5 minute pulse of ethanolamine (1M, pH 8.5). Synbody samples at 100 uM were injected at a flow rate of 30 uL/min over the flow cell surface. Buffer injections identical to the analyte were included throughout the analysis for the purpose of double referencing. The surfaces were regenerated with one 30-s injection of pH 3.0 glycine. The binding level for each injection was determined using Biacore 4000 Evaluation Software.

Supporting Method (SM7)—ELISA Binding Assay for Synbodies

Nunc MaxiSorp flat bottom 96 well ELISA plates (VWR #62409-002) were coated with 100 uL of 1 ug per well of UV inactivated Influenza A PR/8/1934 H1N1 in standard ELISA coating buffer and kept overnight at 4° C. Plates were washed with 1×PBST followed by blocking with 200 uL 6% BSA (ELISA grade fraction V) in 1×PBST for 2 hours at room temperature. Plates were washed twice with 1×PBST and biotin labeled synbodies were added in ELISA dilution buffer (1% BSA+1×PBS+0.05% v/v Tween20) and incubated for 1 hour at room temperature. After washing, 100 uL of 1:100,000 streptavidin-HRP was added and incubated for 1 hour at room temperature. Plates were washed and 100 uL of TMB was added. Plates were incubated in the dark for 8 minutes at room temperature. The reaction was quenched by addition of 100 uL of 0.5 M HCl and read immediately at 450 nm using micro plate reader. ELISA dilution buffer was run as a control on influenza coated wells. Anti-influenza NA (BEI Resources, Cat. No: NR-4540) antibody (5 nM) and unrelated synbody was used as positive and negative control respectively.

Figure 9:
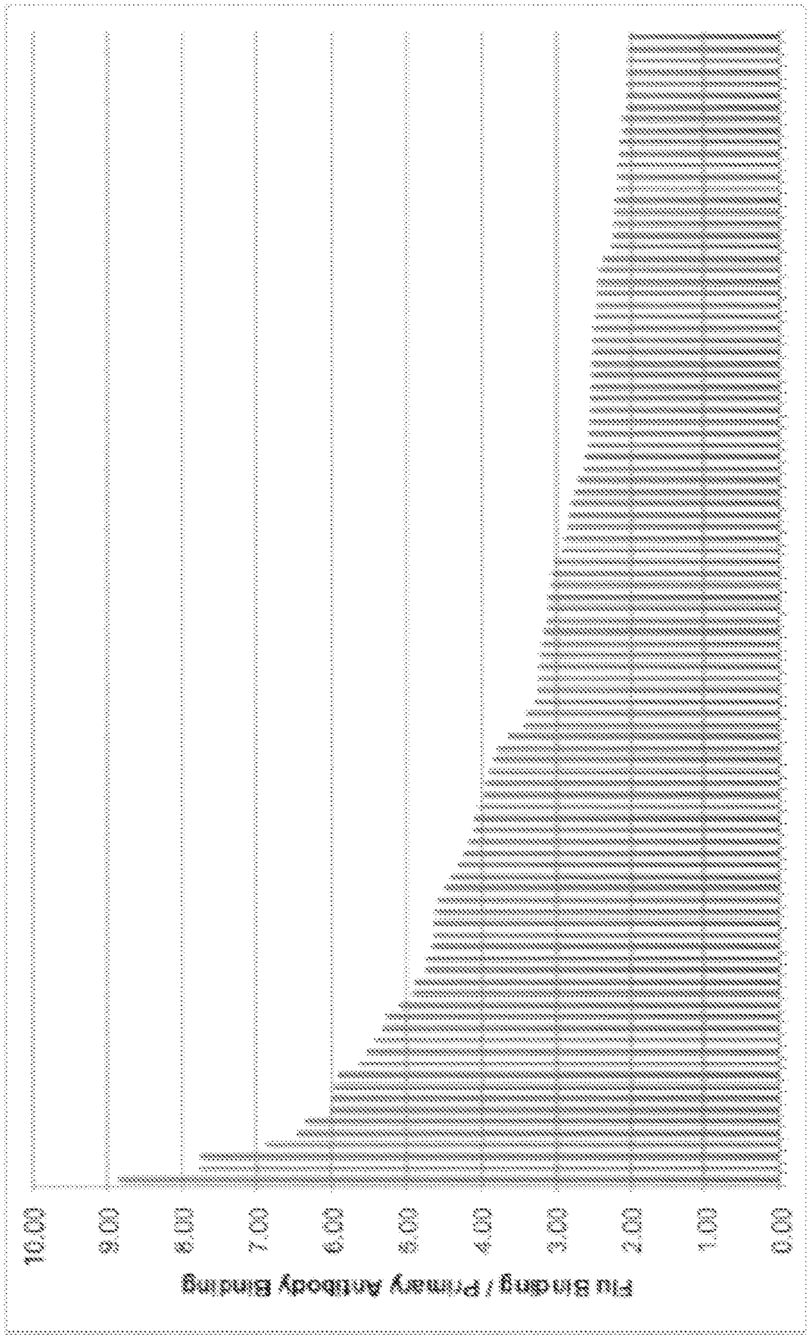
FIG. 9 shows a graphical representation of peptide binding to influenza (1.5×1010 vp/slide) divided by peptide binding to primary antibody.

Referring now to FIG. 9 a graphical representation of peptide binding to influenza (1.5×1010 vp/slide) divided by peptide binding to primary antibody is shown. Median fluorescent intensity was used for each condition.

Figure 10:
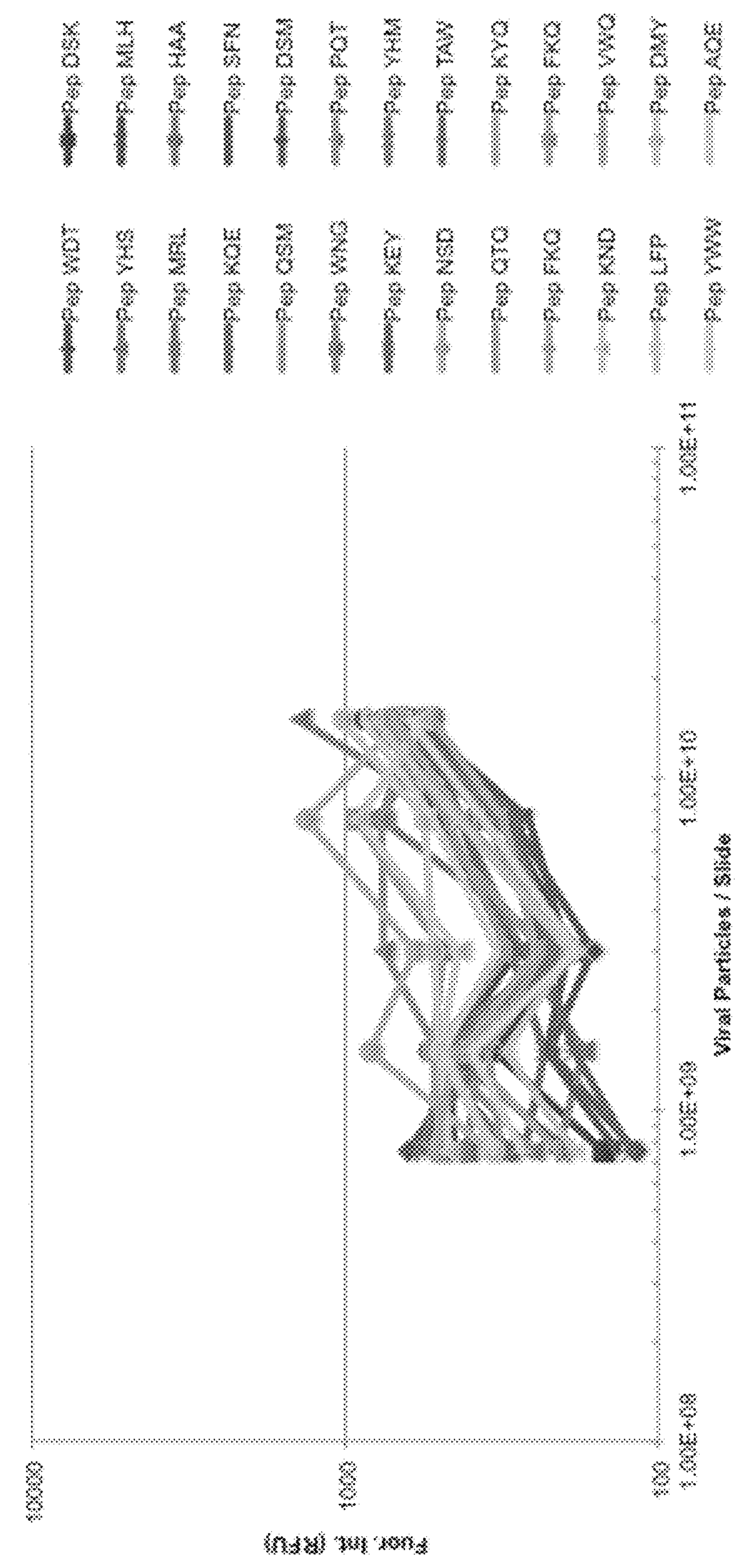
FIG. 10 shows a graphical representation of fluorescent intensity versus virus concentration for candidate peptides with influenza/antibody binding >4.5.

Referring now to FIG. 10 a graphical representation of fluorescent intensity versus virus concentration for candidate peptides with influenza/antibody binding >4.5 is shown.

Figure 11:
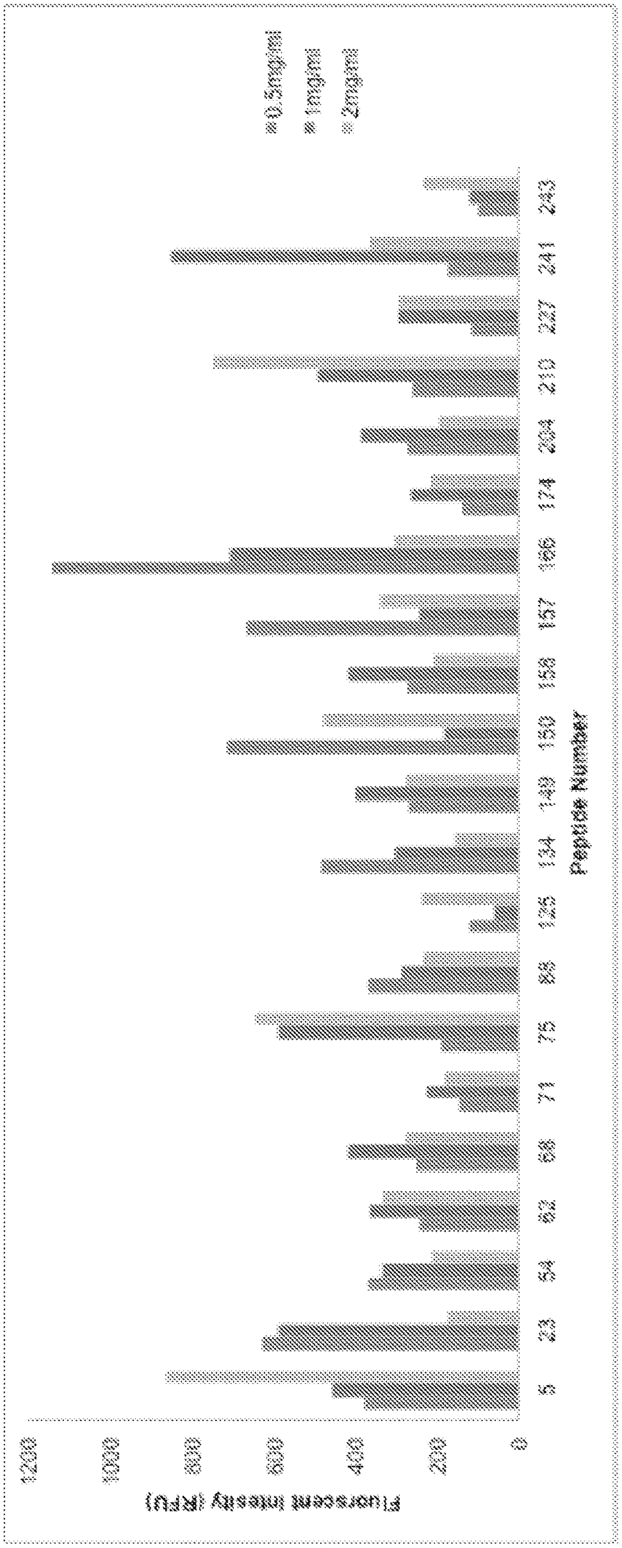
FIG. 11 shows a graphical representation of Influenza binding to candidate peptides immobilized on a microarray.

Referring now to FIG. 11 a graphical representation of Influenza binding to candidate peptides immobilized on a microarray is shown.

Referring now to FIG. 14 HPLC chromatograms of A) opt10 peptide, B) scaffold Sc2, C) reaction mixture at 2 hours, and D) purified synbody opt10-opt10-Sc2 are shown.

Having described properties of synbodies hereinabove, further descriptions of other useful properties of synbodies are described hereinbelow to promote understanding of the advantages and uses of the methods, agents and techniques disclosed herein. In particular it has been found that synbodies inhibit the cytopathic effect of influenza on MDCK cells, that synbodies inhibit influenza replication in MDCK cells, and that the P5-P5 synbody, in particular, binds nucleoprotein.

Figure 15:
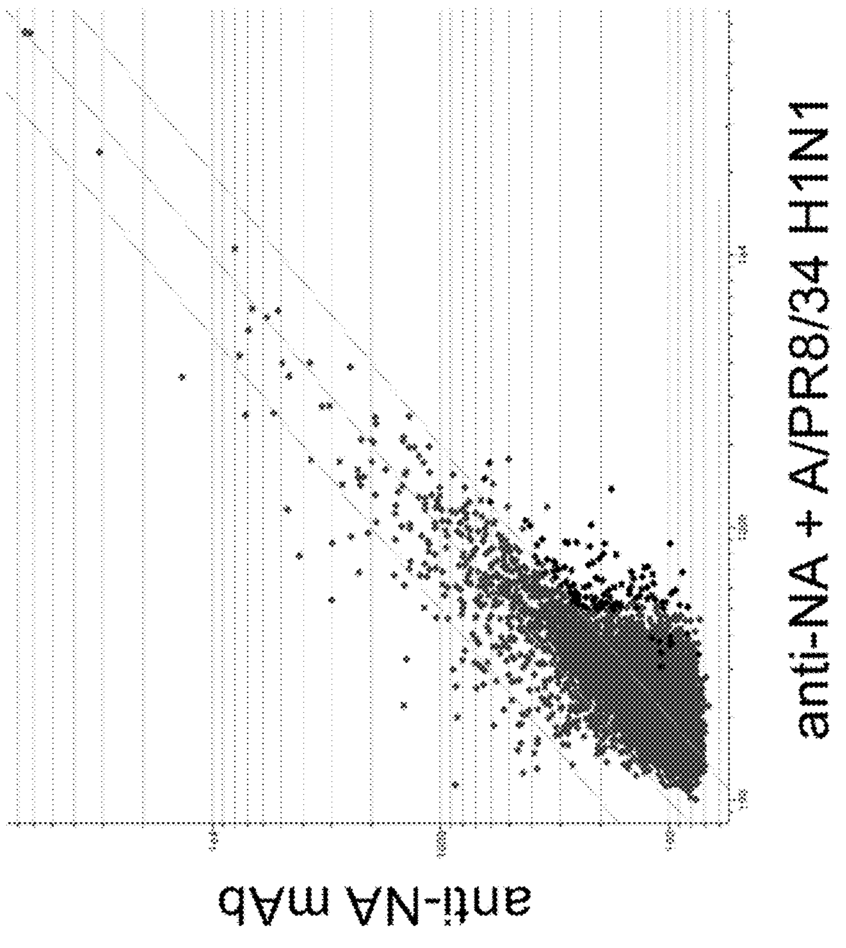
FIG. 15 illustrates a scatter plot of IAV binding (x-axis) versus antibody only binding (y-axis) to 10,000 peptide microarray.
Figure 16:
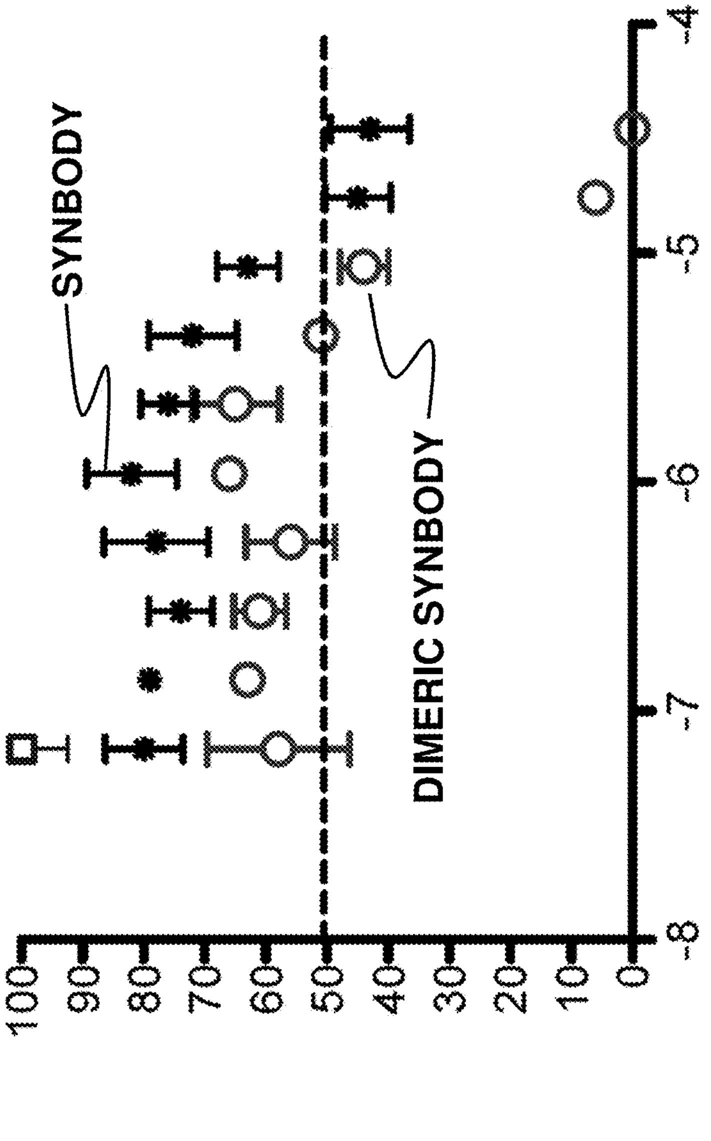
FIG. 16 graphically illustrates a cytopathic effect assay for MDCK cells treated with synbody+A/PR/8/34.

Referring now jointly to FIG. 15 and FIG. 16, FIG. 15 shows a scatter plot of IAV binding (x-axis) versus antibody only binding (y-axis) to 10,000 peptide microarray is illustrated, and FIG. 16 graphically illustrates a cytopathic effect assay for MDCK cells treated with synbody+A/PR/8/34. The illustrated examples support the finding that synbodies inhibit the cytopathic effect of influenza on MDCK cells. Influenza binding peptides were conjugated to a bivalent scaffold (Sc1, as best shown in FIG. 2A) and screened for viral inhibition in an in vitro inhibition assay [3] with A/PR/8/34 H1N1 infected Madin-Darby Canine Kidney (MDCK) cells. A dimeric synbody (FIG. 16—open circles) composed of 2 copies of the same binding peptide (5-5-Sc1) was found to inhibit virus induced cell death (as measured by XTT assay) with an $IC_{50}$ of ~2.5 μM.

Figure 17A:
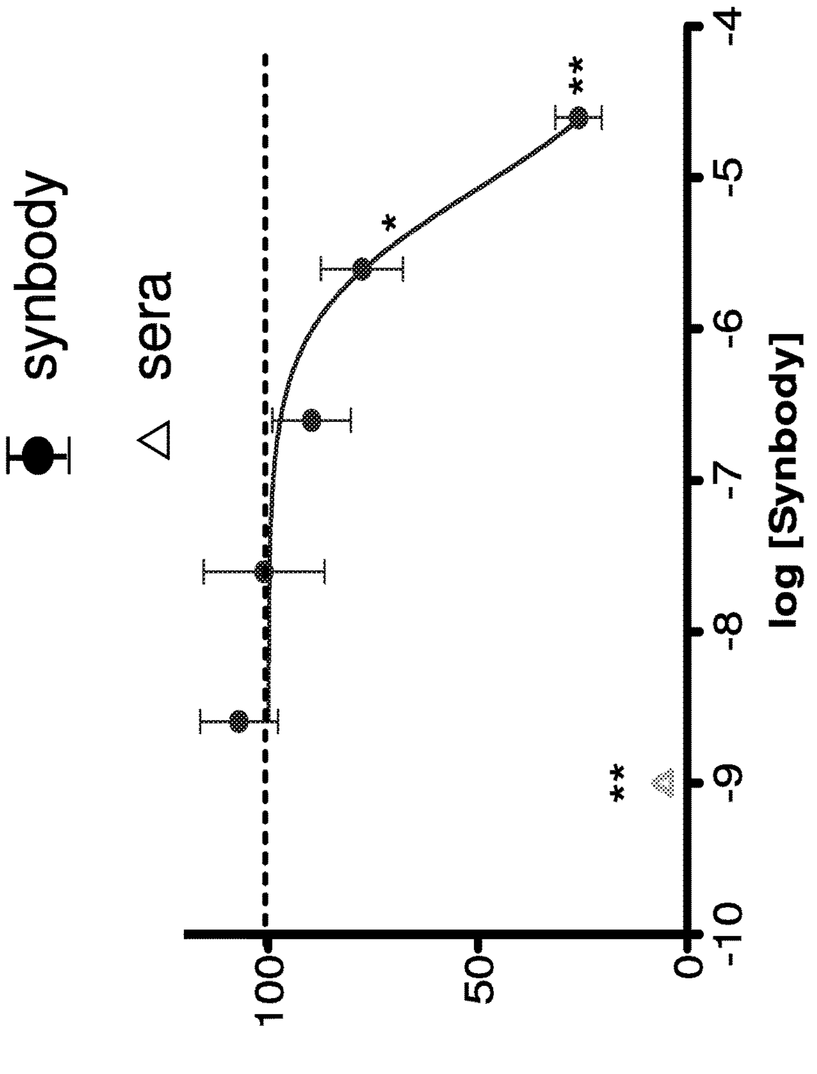
FIG. 17A shows reduction of A/PR/8/34 replication as measured by NA positive cells.
Figure 17B:
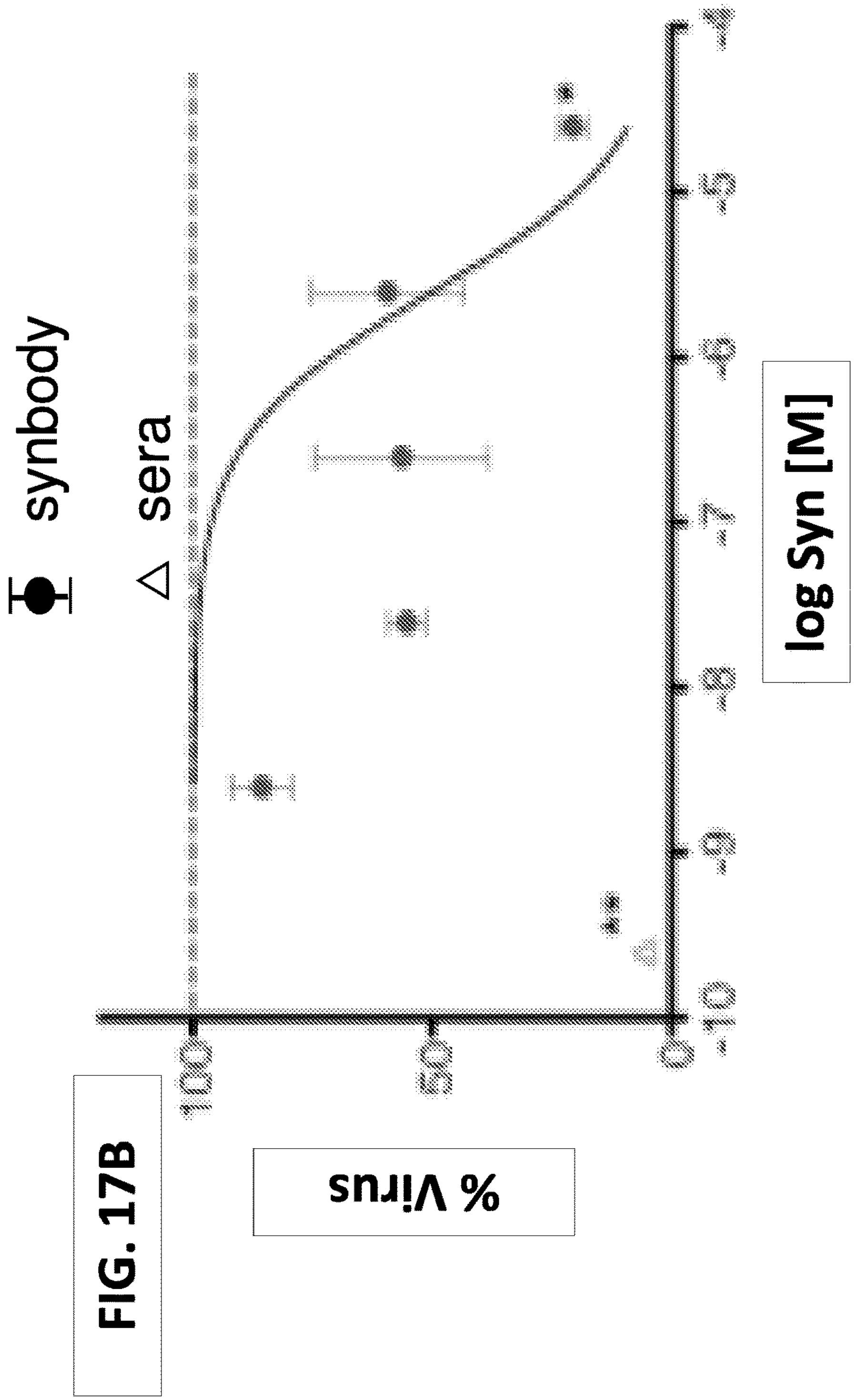
FIG. 17B shows reduction of A/PR/8/34 replication as measured by NP positive cells.

Referring now jointly to FIG. 17A and FIG. 17B, FIG. 17A shows reduction of A/PR/8/34 replication as measured by NA positive cells, and FIG. 17B shows reduction of A/PR/8/34 replication as measured by NP positive cells. The synbody (dot) was compared to a 1:1,000 dilution of sera from mice immunized with A/PR/8/1934 (triangle). *p<0.05, p<0.01. The illustrated examples support the finding that synbodies inhibit influenza replication in MDCK cells. To directly measure inhibition of A/PR/8/34 replication, we tested P5-P5-Sc2 inhibitory activity in a plaque reduction assay adapted from [4]. In this assay, P5-P5-Sc2 and A/PR/8/34 were added to MDCK cells at a multiplicity of infection of 0.01 for 2 hours before a layer of Avicel® microcrystalline cellulose was added. (Avicel® is a microcrystalline cellulose product commercially available from FMC BioPolymer 1735 Market Street Philadelphia, Pa. 19103.) Cells were incubated for 24 hours, fixed, permeabilized and infected cells were detected with either an anti-neuraminidase (NA) or anti-NP monoclonal antibody. Influenza positive plaques were counted and plaque inhibition was plotted as a function of synbody concentration (as best seen in FIG. 17B). Sera from mice previously immunized with A/PR/8/34 was used as a positive control and showed virtually complete inhibition of virus replication. The synbody inhibited virus replication with an $IC_{50}$ ~2.5 μM, in good agreement with the cytopathic effect assay described above with reference to FIG. 16**B, although inhibition did not fit to a classical inhibition model (black line). The synbody was then tested against two additional influenza strains, A/CA/7/2009 H1N1 and A/Sydney/5/1997 H3N2, and had similar inhibition constants despite the differences in each strain (Table 4).

TABLE 4

Viral yield reduction as measured by NP positive cells.

| | $IC_{50}$ |
|---|---|
| A/PR/8/34 H1N1 | 2.5 μM |
| A/CA/7/09 H1N1 | 2.5 μM |
| A/Sydney/5/97 H3N2 | 2.5 μM |

Figure 18A:
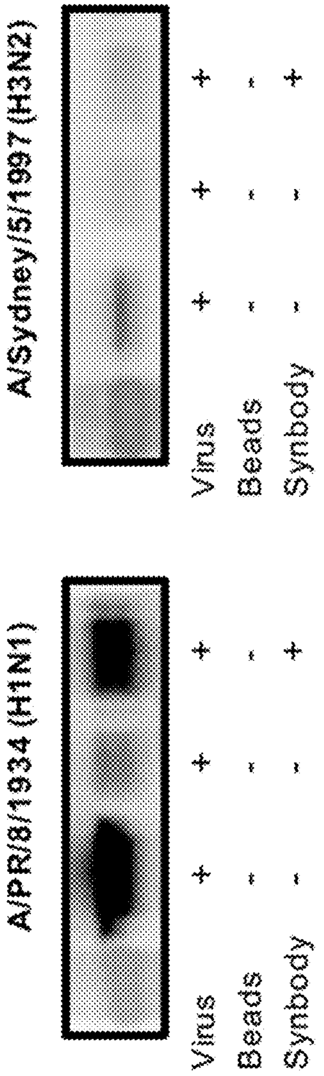
FIG. 18A illustrates Pull-down of NP from viral lysates using P5-P5-Sc2 synbody, where the synbody was added to either A/PR/8/34 or A/Sydney/5/97 lysates and captured NP was detected by anti-NP antibody.
Figure 18B:
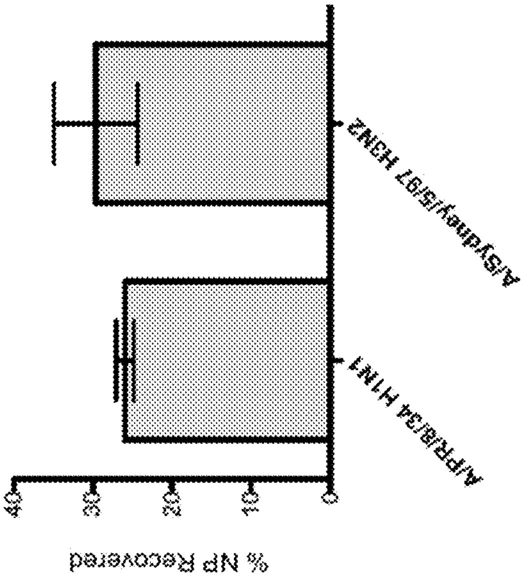
FIG. 18B illustrates percent of NP recovered by the synbody for each lysate.

Referring now jointly to FIG. 18A and FIG. 18B, FIG. 18A illustrates Pull-down of NP from viral lysates using P5-P5-Sc2 synbody, where the synbody was added to either A/PR/8/34 or A/Sydney/5/97 lysates and captured NP was detected by anti-NP antibody, and FIG. 18B illustrates percent of NP recovered by the synbody for each lysate. These examples support the finding that the P5-P5 synbody binds nucleoprotein. As the synbody was developed using the intact influenza virus, we believed that hemagglutinin (HA) was the likely target. However, P5-P5-Sc2 did not inhibit hemagglutination of A/PR/8/34. This led us to investigate which viral protein the synbody bound. We tested P5-P5-Sc2 in a pull-down assay against A/PR/8/34 H1N1 and A/Sydney/5/1997 H3N2 viral lysate. As NP is one of the most abundant viral proteins, we probed the membrane with an anti-NP antibody and found that the synbody pulled-down NP from both lysates (FIG. 18). NP is highly conserved amongst influenza strains and is 100% conserved between these two strains. As seen in FIG. 18B, the percent of NP recovered from each lysate is roughly the same.

Figure 19A:
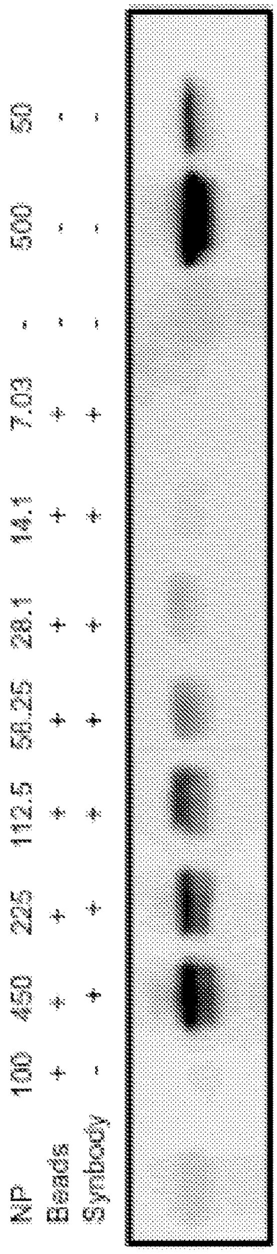
FIG. 19A is a Western blot of NP pulled down from samples of purified NP using P5-P5-Sc2.
Figure 19B:
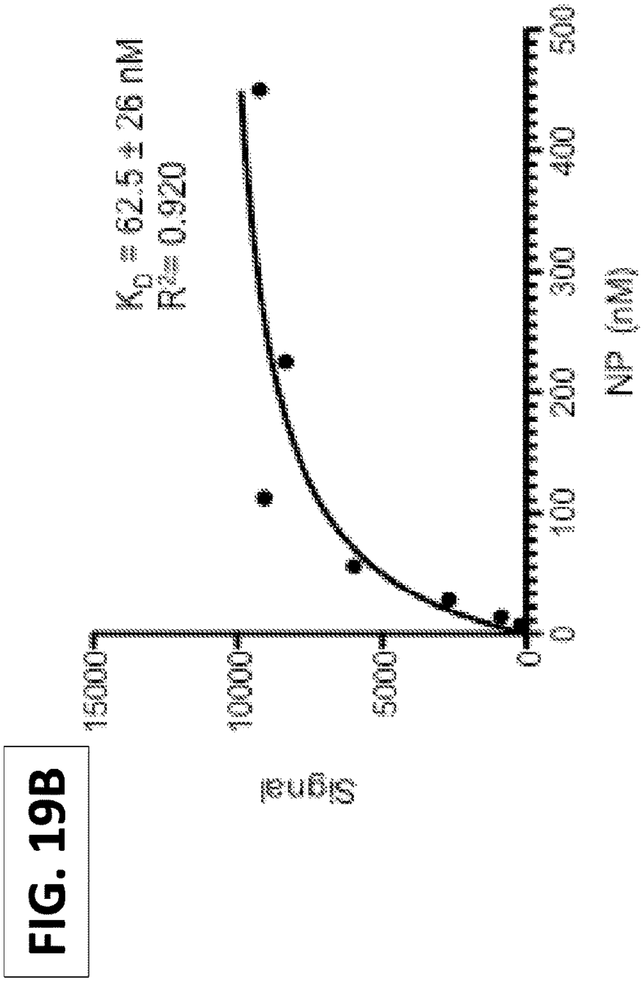
FIG. 19B shows the determination of binding affinity by pull-down of NP pulled down in FIG. 19A.
Figure 19C:
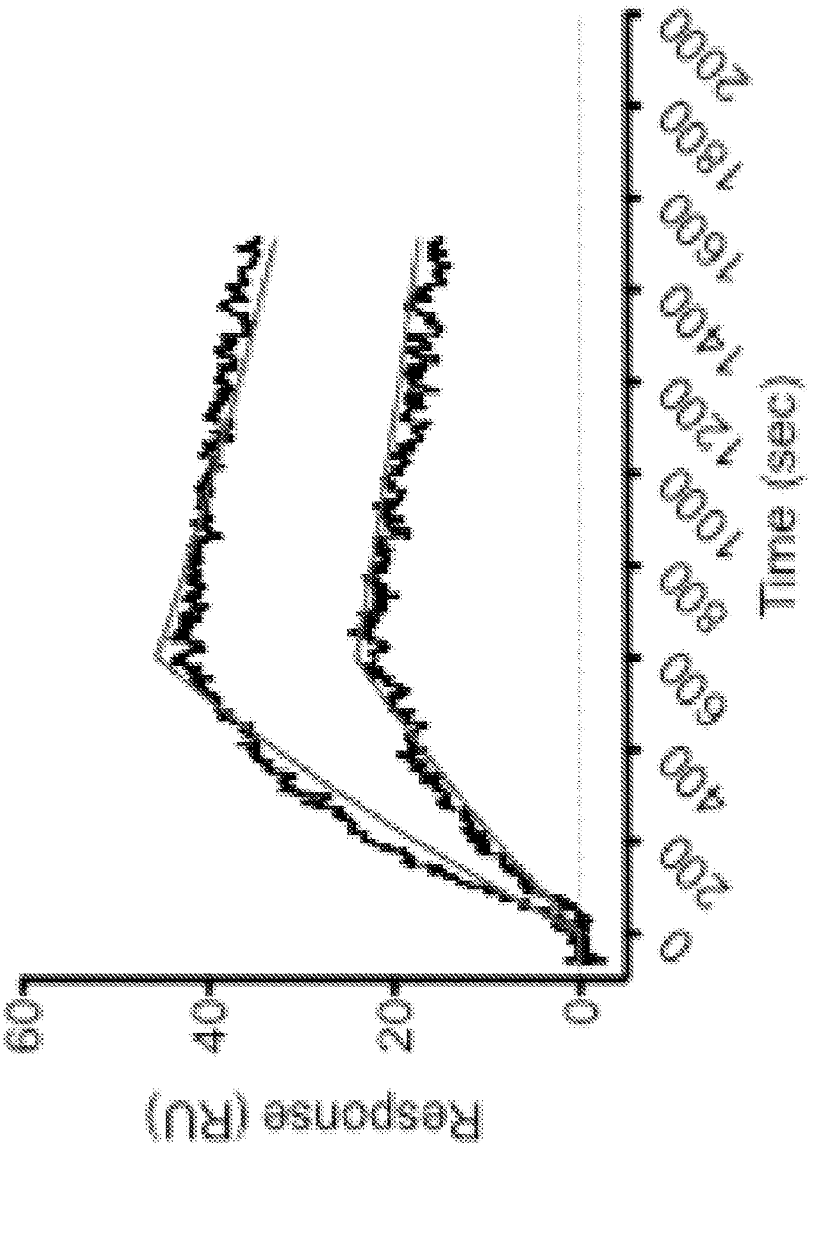
FIG. 19C shows SPR sensorgrams of 0.5 and 1.0 nM NP binding to P5-P5-Sc2.

Referring now jointly to FIG. 19A, FIG. 19B and FIG. 19C, we then sought to estimate the binding affinity of P5-P5-Sc2 for NP. As shown in the Western plot of FIG. 19A the synbody was used to pull down NP from increasing concentration solutions of purified NP. As shown in FIG. 19B, recovered NP was quantified and the KD was determined to be 62±26 nM. AS illustrated in FIG. 19 C, SPR sensorgrams of 0.5 and 1.0 nM NP binding to P5-P5-Sc2As. NP forms oligomers at higher concentrations, we screened 0.5 and 1.0 nM solutions of purified NP by SPR against immobilized P5-P5-Sc2 and estimated the KD at ~30 nM (FIG. 19C). Low concentrations were used to ensure NP existed as a monomer in solution.

Although the invention has been described with reference to the presently preferred embodiments, it should be understood that various modifications can be made without departing from the invention. Unless otherwise apparent from the context any step, element, embodiment, feature or aspect of the invention can be used with any other. All publications (including GenBank or Swiss-Prot Accession numbers and the like), patents and patent applications cited are herein incorporated by reference in their entirety for all purposes to the same extent as if each individual publication, patent and patent application was specifically and individually indicated to be incorporated by reference in its entirety for all purposes. If more than one version of a sequence is associated with a deposit number at different times, the version associated with the deposit number at the time of filing the application is meant.

REFERENCES

1. Jonges, M.; Liu, W. M.; van der Vries, E.; Jacobi, R.; Pronk, I.; Boog, C.; Koopmans, M.; Meijer, A.; Soethout, E. *Journal of Clinical Microbiology* 2010, 48, 928.
2. Tarus, B.; Chevalier, C.; Richard, C.-A.; Delmas, B.; Di Primo, C.; Slama-Schwok, A. Plos One 2012, 7, e30038.
3. Grund S, Adams O, Wählisch S, Schweiger B (2011) Comparison of hemagglutination inhibition assay, an ELISA-based micro-neutralization assay and colorimetric microneutralization assay to detect antibody responses to vaccination against influenza A H1N1 2009 virus. Journal of Virological Methods 171: 369-373.
4. Matrosovich M, Matrosovich T, Garten W, Klenk H D (2006) New low-viscosity overlay medium for viral plaque assays. Virol J 3: 63.

What is claimed is:

1. An agent comprising a first peptide having an amino acid sequence comprising a first mutant of SEQ. ID NO: 1 and a second mutant of SEQ ID NO: 1, wherein the first and second mutants are linked and consist of linked mutant peptides SEQ. ID NO: 2-SEQ. ID NO: 2, SEQ. ID NO: 3-SEQ. ID NO: 3, SEQ. ID NO: 5-SEQ. ID NO: 5, SEQ. ID NO: 7-SEQ. ID NO: 7, SEQ. ID NO: 8-SEQ. ID NO: 8, SEQ. ID NO: 9-SEQ. ID NO: 9, SEQ. ID NO: 10-SEQ. ID NO: 10, SEQ. ID NO: 11-SEQ. ID NO: 11, SEQ. ID NO: 12-SEQ. ID NO: 12, or SEQ. ID NO: 15-SEQ. ID NO: 15.

2. The agent of claim 1 wherein the first and second mutant peptides are linked to a scaffold structure to synthesize a composition having an affinity for a target molecule.

3. The agent as in claim 1 or 2 wherein the synthesized composition has an affinity for influenza viruses.

4. The agent as in claim 2 or 3 wherein the scaffold structure has the structure:

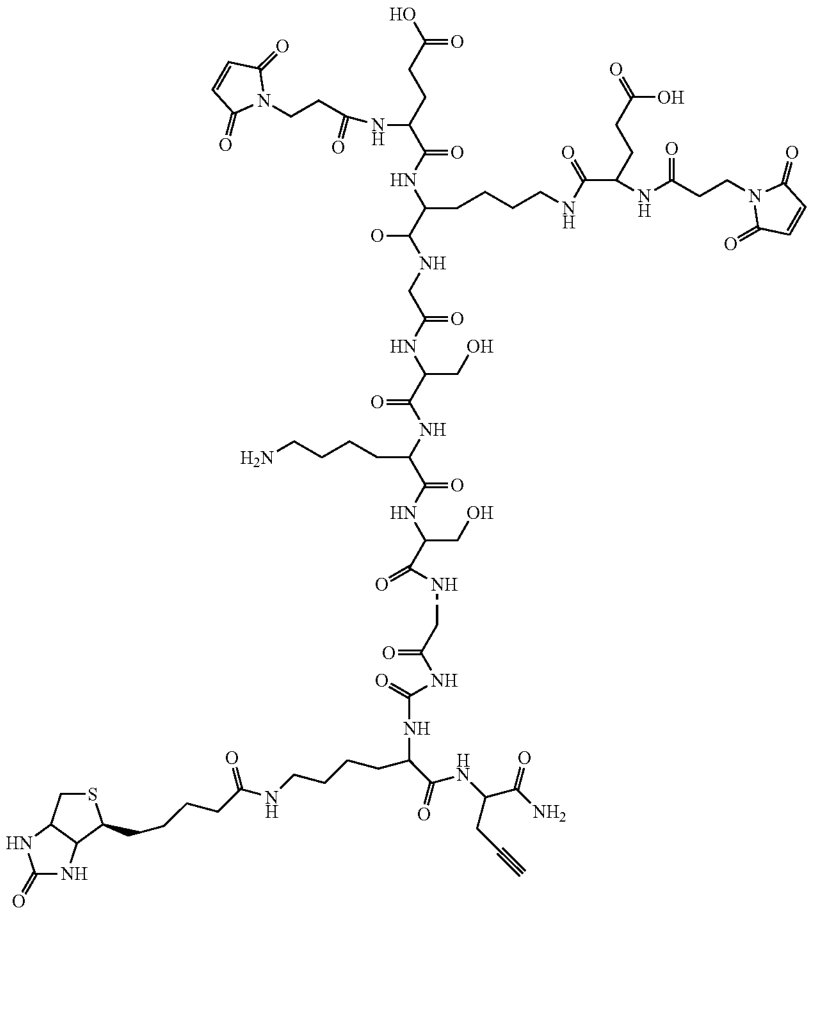 [SMILES: C#CCC(NC(=O)C(CCCCNC(=O)CCCC[C@@H]1SCC2NC(=O)NC21)NC(=O)NC(=O)CNC(=O)C(CO)NC(=O)C(CCCCN)NC(=O)C(CO)NC(=O)CNC(O)C(CCCCNC(=O)C(CCC(=O)O)NC(=O)CCN1C(=O)C=CC1=O)NC(=O)C(CCC(=O)O)NC(=O)CCN1C(=O)C=CC1=O)C(N)=O]

5. The agent as in claim 2 or 3 wherein the scaffold structure has the structure:
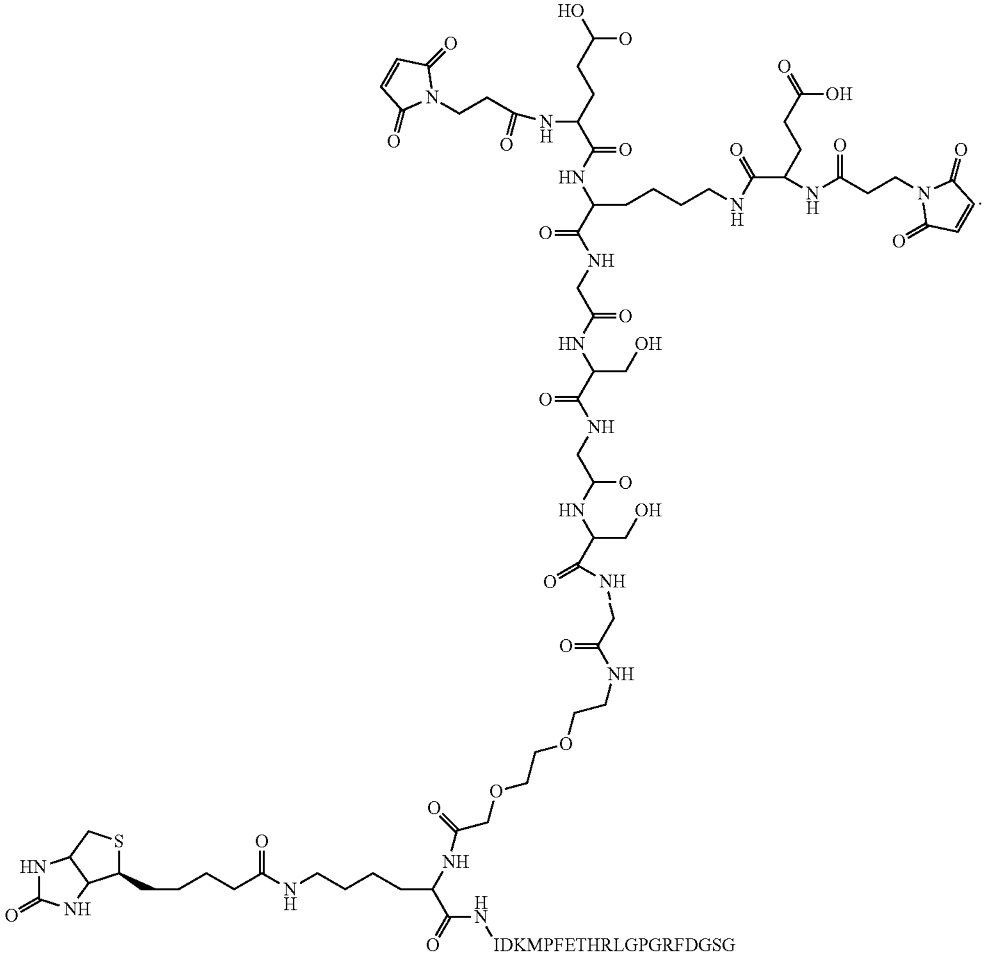
6. A composition comprising or consisting of SEQ ID NO: 2, SEQ. ID NO: 3, SEQ. ID NO: 4, SEQ. ID NO: 5, SEQ. ID NO: 6, SEQ. ID NO: 7, SEQ. ID NO: 8, SEQ. ID NO: 9, SEQ. ID NO: 10, SEQ. ID NO: 11, SEQ. ID NO: 12, SEQ. ID NO: 13, SEQ. ID NO: 14 or SEQ. ID NO: 15.
7. A composition comprising or consisting of the structure:
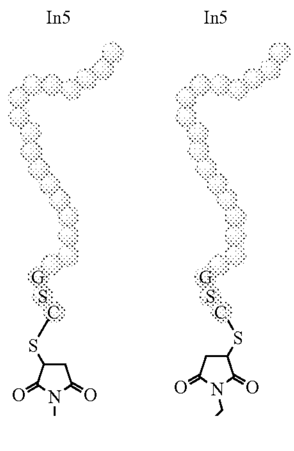
-continued
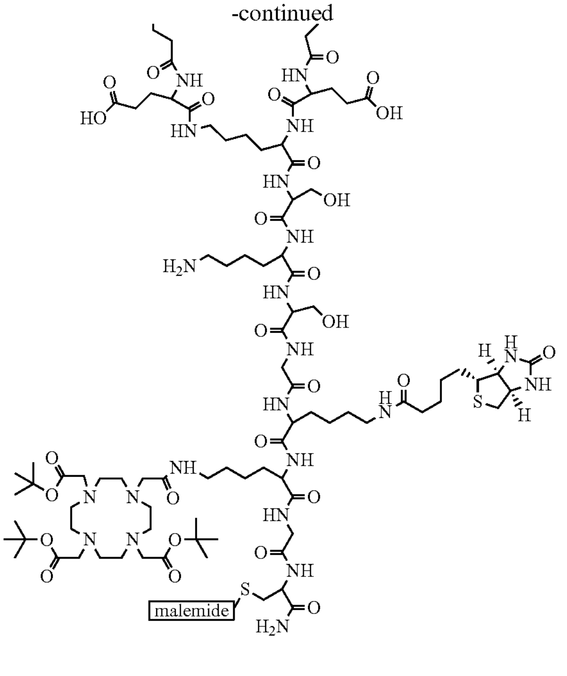

where In5 comprises or consists of SEQ ID NO: 2, SEQ. ID NO: 3, SEQ. ID NO: 4, SEQ. ID NO: 5, SEQ. ID NO: 6, SEQ. ID NO: 7, SEQ. ID NO: 8, SEQ. ID NO: 9, SEQ. ID NO: 10, SEQ. ID NO: 11, SEQ. ID NO: 12, SEQ. ID NO: 13, SEQ. ID NO: 14 or SEQ. ID NO: 15.

8. A therapeutic agent for influenza comprising a first peptide having an amino acid sequence comprising a first mutant of SEQ. ID NO: 1 and a second mutant of SEQ ID NO: 1, wherein the first and second mutants are linked and consist of linked mutant peptides SEQ. ID NO: 2-SEQ. ID NO: 2, SEQ. ID NO: 3-SEQ. ID NO: 3, SEQ. ID NO: 5-SEQ. ID NO: 5, SEQ. ID NO: 7-SEQ. ID NO: 7, SEQ. ID NO: 8-SEQ. ID NO: 8, SEQ. ID NO: 9-SEQ. ID NO: 9, SEQ. ID NO: 10-SEQ. ID NO: 10, SEQ. ID NO: 11-SEQ. ID NO: 11, SEQ. ID NO: 12-SEQ. ID NO: 12, or SEQ. ID NO: 15-SEQ. ID NO: 15; wherein the first and second mutant peptides are linked to a scaffold structure to synthesize a composition having an affinity for influenza viruses; and wherein the agent further comprises a therapeutic molecule linked to the synthesized composition.

* * * * *

SEQUENCE LISTING

<160> NUMBER OF SEQ ID NOS: 36

<210> SEQ ID NO 1
<211> LENGTH: 20
<212> TYPE: PRT
<213> ORGANISM: Artificial Sequence
<220> FEATURE:
<223> OTHER INFORMATION: Synthetic Antibody

<400> SEQUENCE: 1

Cys Ser Gly Asp Met Tyr Glu Tyr Asn Pro Phe Gln Gly Asn His Ile
1 5 10 15

Tyr Asn Lys Lys
20

<210> SEQ ID NO 2
<211> LENGTH: 20
<212> TYPE: PRT
<213> ORGANISM: Artificial Sequence
<220> FEATURE:
<223> OTHER INFORMATION: Synthetic Antibody

<400> SEQUENCE: 2

Cys Ser Gly Asp Met Tyr Arg Tyr Asn Pro Phe Gln Gly Asn His Ile
1 5 10 15

Tyr Asn Lys Lys
20

<210> SEQ ID NO 3
<211> LENGTH: 20
<212> TYPE: PRT
<213> ORGANISM: Artificial Sequence
<220> FEATURE:
<223> OTHER INFORMATION: synthetic antibody

<400> SEQUENCE: 3

Cys Ser Gly Arg Met Tyr Glu Tyr Asn Pro Phe Gln Gly Asn His Ile
1 5 10 15

Tyr Asn Lys Lys
20

<210> SEQ ID NO 4
<211> LENGTH: 20
<212> TYPE: PRT
<213> ORGANISM: Artificial Sequence
<220> FEATURE:
<223> OTHER INFORMATION: synthetic antibody

<400> SEQUENCE: 4

Cys Ser Gly Asp Met Tyr Pro Tyr Asn Pro Phe Gln Gly Asn His Ile
1 5 10 15

Tyr Asn Lys Lys
20

<210> SEQ ID NO 5
<211> LENGTH: 20
<212> TYPE: PRT
<213> ORGANISM: Artificial Sequence
<220> FEATURE:
<223> OTHER INFORMATION: Synthetic antibody

<400> SEQUENCE: 5

Cys Ser Gly Arg Met Tyr Pro Tyr Asn Pro Phe Gln Gly Asn His Ile
1 5 10 15

-continued

```
Tyr Asn Lys Lys
            20


<210> SEQ ID NO 6
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 6

Cys Ser Gly Arg Met Tyr Arg Tyr Asn Pro Phe Gln Gly Asn His Ile
1               5                   10                  15

Tyr Asn Lys Lys
            20


<210> SEQ ID NO 7
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 7

Cys Ser Gly Asp Met Tyr Glu Tyr Asn Pro Phe Gln Gly Asn His Ile
1               5                   10                  15

Tyr Arg Lys Lys
            20


<210> SEQ ID NO 8
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 8

Cys Ser Gly Arg Met Tyr Pro Tyr Asn Pro Phe Gln Gly Asn His Ile
1               5                   10                  15

Tyr Arg Lys Lys
            20


<210> SEQ ID NO 9
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 9

Cys Ser Gly Thr Met Tyr Glu Tyr Asn Pro Phe Gln Gly Asn His Ile
1               5                   10                  15

Tyr Asn Lys Lys
            20


<210> SEQ ID NO 10
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 10

Cys Ser Gly Arg Met Tyr Pro Tyr Arg Pro Phe Gln Gly Asn His Ile
1               5                   10                  15
```

```
Tyr Arg Lys Lys
            20


<210> SEQ ID NO 11
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 11

Cys Ser Gly Arg Met Tyr Pro Tyr Arg Pro Phe Gln Gly Asn His Ile
1               5                   10                  15

Tyr Arg Lys Lys
            20


<210> SEQ ID NO 12
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 12

Cys Ser Gly Thr Met Tyr Pro Tyr Arg Pro Phe Gln Gly Asn His Ile
1               5                   10                  15

Tyr Arg Lys Lys
            20


<210> SEQ ID NO 13
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 13

Cys Ser Gly Arg Met Tyr Pro Tyr Arg Pro Phe Gln Arg Lys His Ile
1               5                   10                  15

Tyr Arg Lys Lys
            20


<210> SEQ ID NO 14
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 14

Cys Cys Ser Gly Asp Arg Tyr Glu Tyr Asn Pro Phe Gln Gly Lys His
1               5                   10                  15

Ile Tyr Asn Lys
            20


<210> SEQ ID NO 15
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 15

Cys Ser Gly Arg Met Tyr Glu Tyr Asn Pro Phe Gln Gly Lys His Ile
```

-continued

```
1               5                   10                  15

Tyr Arg Lys Lys
            20


<210> SEQ ID NO 16
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 16

Cys Ser Gly Asp Ser Pro Met Gly Tyr Tyr His Gln Lys Thr Ser Pro
1               5                   10                  15

Trp Ala Asp Lys
            20


<210> SEQ ID NO 17
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 17

Cys Ser Gly Gln Phe Ser Ala Lys Lys Tyr Trp Glu Ile Lys Pro Met
1               5                   10                  15

Asp Tyr Trp Lys
            20


<210> SEQ ID NO 18
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 18

Cys Ser Gly Gln Tyr Ser Gln Gln Ser Ser Ser Tyr Gly Gln Gln Met
1               5                   10                  15

Phe Lys Lys Glu
            20


<210> SEQ ID NO 19
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 19

Cys Ser Gly Ala Gln Glu Trp Ala Ala Lys Ser Tyr Lys Trp Asn Lys
1               5                   10                  15

Asp Gly Tyr Leu
            20


<210> SEQ ID NO 20
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 20
```

-continued

```
Cys Ser Gly Asp Met His Trp Gly Tyr Gln Asp Gly Lys Thr Leu Val
1               5                   10                  15

Pro Thr Ser Lys
            20


<210> SEQ ID NO 21
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 21

Cys Ser Gly Asp Pro Thr His Ala Thr Glu Pro Lys Arg Tyr Glu Ala
1               5                   10                  15

Tyr Asn Asp His
            20


<210> SEQ ID NO 22
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 22

Cys Ser Gly Glu Met Trp Ala Ile Met Pro Pro Ile Ile Lys Pro Asp
1               5                   10                  15

Asn Lys Gly His
            20


<210> SEQ ID NO 23
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 23

Cys Ser Gly His Asn Ile Tyr Ala Gln Tyr Gly Tyr Pro Tyr Asp His
1               5                   10                  15

Met Tyr Glu Gly
            20


<210> SEQ ID NO 24
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 24

Cys Ser Gly Lys Asp His Asn Ala Gln Asp Gln Glu Ser Val His Trp
1               5                   10                  15

Lys Tyr Lys Gly
            20


<210> SEQ ID NO 25
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 25
```

Cys Ser Gly Lys Arg Tyr Leu Gln Lys Gly Lys Gly Ala Leu Arg Gly
1 5 10 15

Leu Tyr Ile Phe
20

<210> SEQ ID NO 26
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 26

Cys Ser Gly Lys Ser Gln Glu Ile Gly Asp Pro Asp Asp Ile Trp Asn
1 5 10 15

Gln Met Lys Trp
20

<210> SEQ ID NO 27
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 27

Cys Ser Gly Lys Thr Glu His Tyr Met Pro Asn Asn Asn Thr Phe Gly
1 5 10 15

Tyr Glu Tyr Glu
20

<210> SEQ ID NO 28
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 28

Cys Ser Gly Leu Leu His Glu Leu Pro Asp Asp Tyr Glu Lys Ile Asn
1 5 10 15

Pro Gln Lys Tyr
20

<210> SEQ ID NO 29
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 29

Cys Ser Gly Leu Leu Tyr His Phe Lys Val Gly Leu Arg Thr Met Lys
1 5 10 15

Ile Ser Met Met
20

<210> SEQ ID NO 30
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 30

Cys Ser Gly Met Lys Gln Pro Lys His Asn Lys Ile Asn Asp Asn Pro
1 5 10 15

Lys Ala Tyr Glu
20

<210> SEQ ID NO 31
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 31

Cys Ser Gly Asn Glu Thr Ala Pro Asp Asn Thr Tyr Arg Tyr Lys Gln
1 5 10 15

Ser Ala Gln Lys
20

<210> SEQ ID NO 32
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 32

Cys Ser Gly Ser Phe Asn Gln Glu Tyr Phe Pro Tyr Pro Met Ile Asp
1 5 10 15

Tyr Leu Lys Lys
20

<210> SEQ ID NO 33
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 33

Cys Ser Gly Thr Ala Asn Glu Leu Leu Tyr Tyr Lys Asn Tyr Gly Val
1 5 10 15

Lys Asn Pro Lys
20

<210> SEQ ID NO 34
<211> LENGTH: 20
<212> TYPE: PRT
<213> ORGANISM: ARTIFICIAL SEQUENCE
<220> FEATURE:
<223> OTHER INFORMATION: Synthetic antibody

<400> SEQUENCE: 34

Cys Ser Gly Thr Glu Glu Lys Tyr Ile Asn Asp Ser Asn Phe Ala Asp
1 5 10 15

Glu Lys Gly His
20

<210> SEQ ID NO 35
<211> LENGTH: 6
<212> TYPE: PRT
<213> ORGANISM: ARTIFICIAL SEQUENCE
<220> FEATURE:
<223> OTHER INFORMATION: Synthetic antibody -continued

```
<400> SEQUENCE: 35

Gly Ser Gly Lys Ser Gly
1               5


<210> SEQ ID NO 36
<211> LENGTH: 19
<212> TYPE: PRT
<213> ORGANISM: ARTIFICIAL SEQUENCE
<220> FEATURE:
<223> OTHER INFORMATION: Synthetic antibody

<400> SEQUENCE: 36

Ile Met Lys Pro Phe Glu Thr His Arg Leu Gly Pro Glu Arg Phe Asp
1               5                   10                  15

Gly Ser Cys
```